United States Patent
Al-Abed et al.

(10) Patent No.: US 6,492,428 B1
(45) Date of Patent: Dec. 10, 2002

(54) COMPOUNDS HAVING MIF ANTAGONIST ACTIVITY

(75) Inventors: Yousef Al-Abed, Locust Valley, NY (US); Richard J. Bucala, Cos Cob, CT (US); Robert A. Mitchell, Great Neck, NY (US); Peter Senter, Seattle, WA (US)

(73) Assignee: The Picower Institute for Medical Research, Manhasset, NY (US)

( * ) Notice: Subject to any disclaimer, the term of this patent is extended or adjusted under 35 U.S.C. 154(b) by 0 days.

(21) Appl. No.: 09/625,829

(22) Filed: Jul. 26, 2000

(51) Int. Cl.[7] .......................... A61K 31/17; A61K 31/12
(52) U.S. Cl. ...................................... 514/675; 514/598
(58) Field of Search ............................... 514/598, 675

(56) References Cited

U.S. PATENT DOCUMENTS 6,030,615 A    2/2000   Bucala et al.

OTHER PUBLICATIONS

Gennaro, Ed., Remington's Pharmaceutical Sciences, 18th Ed., 1990, p. 1120.*
Ramsay et al. In Vitro Effects of Acetaminophen Metabolites and Analogs on the Respiration of Mouse Liver Mitochondria, Archives of Biochemistry and Biophysics, vol. 273 No. 2, pp. 449–457, Sep. 1989.*
Taylor et al. Dorland's Ilustrated Medical Dictionary, 27th Ed., 1988, p. 703.*
Swope, M.D., et al., "Macrophage Migration Inhibitory Factor: Cytokine, Hormone, or Enzyme?", Rev. Physiol. Biochem. Pharmacol., vol. 139, pp. 1–32 (1999).
Metz, C.N., et al., "Role of Macrophage Migration Inhibitory Factor in the Regulation of the Immune Response", Advances in Immunology, vol. 66, pp. 197–223 (1997).
Bucala, R., "MIF Rediscovered: Cytokine, Pituitary Hormone, and Glucocorticoid–Induced Regulator of the Immune Response", The FASEB Journal, vol. 10, pp. 1607–1613 (1996).
George, M., et al., "In vitro Cell Migration as a Model for Delayed Hypersensitivity", Proc. Soc. Exp. Biol. Med., vol. 111, pp. 514–521 (1962).
Weiser, W.Y., et al., "Studies on Human Migration Inhibitory Factor: Characterization of Three Molecular Species", The Journal of Immunology, vol. 126, No. 5, pp. 1958–1962 (1981).
Bloom, B.R., et al., "Mechanism of a Reaction in Vitro Associated with Delayed–Type Hypersensitivity", Science, vol. 153, pp. 80–82 (1966).
David, J.R., "Delayed Hypersensitivity In Vitro: Its Mediation by Cell–Free Substances Formed by Lymphoid Cell–Antigen Interaction", Proc. Natl. Acad. Sci. USA, vol. 56, pp. 72–77 (1966).

(List continued on next page.)

Primary Examiner—Russell Travers
Assistant Examiner—Mojdeh Bahar
(74) Attorney, Agent, or Firm—Piper Rudnick LLP; Steven B. Kelber

(57) ABSTRACT

There are disclosed methods of use and pharmaceutical compositions for two related genera of low molecular weight compounds comprising optionally substituted iminoquinone or orthoquinone ring systems. The compounds have MIF (macrophage migration inhibitory factor) antagonist activity and find utility as such. For example, the compounds are useful for treating a variety of diseases involving inflammatory activity or pro-inflammatory cytokine responses, such as autoimmune diseases (including rheumatiod arthritis, insulin-dependent diabetes, multiple sclerosis, graft versus host disease, lupus syndromes), asthma, arthritis, EAE, ARDS, psoriasis, interleukin-2 toxicity, proliferative vascular disease, and various forms of sepsis and septic shock, and other conditions characterized by underlying MIF responses including, for instance, tumor growth and neovascularization (angiogenesis).

11 Claims, 8 Drawing Sheets

OTHER PUBLICATIONS

Nathan, C.F., et al., "Characterization of a Lymphocyte Factor Which Alters Macrophage Functions", The Journal of Experimental Medicine, vol. 137, pp. 275–290 (1973).

Nathan, C.F., et al., "Alterations of Macrophage Functions by Mediators from Lymphocytes", The Journal of Experimental Medicine, vol. 133, pp. 1356–1376 (1971).

Churchill, W.H., et al., "Macrophage Activated as Suspension Cultures with Lymphocyte Mediators Devoid of Antigen Become Cytotoxic for Tumor Cells", The Journal of Immunology, vol. 115, No. 3, pp. 781–786 (1975).

McInnes, A., et al., "Interleukin 4 Induces Cultured Monocytes/Macrophages to form Giant Multinucleated Cells", J. Exp. Med., vol. 167, pp. 598–611 (1988).

Thurman, G.B., et al., "MIF–Like Activity of Natural and Recombinant Human Interferon–γ and Their Neutralization by Monoclonal Antibody", The Journal of Immunology, vol. 134, No. 1, pp. 305–309 (1985).

Weiser, W.Y., et al., "Molecular Cloning of a cDNA Encoding a Human Macrophage Migration Inhibitory Factor", Proc. Natl. Acad. Sci. USA, vol. 86, pp. 7522–7526 (1989).

Weiser, W.Y., et al., "Human Recombinant Migration Inhibitory Factor Activates Human Macrphages to Kill *Leishmania donovani*", The Journal of Immunology, vol. 147, No. 6, pp. 2006–2011 (1991).

Pozzi, L., et al., "Human Recombinant Migration Inhibitory Factor Activates Human Macrophages to Kill Tumor Cells", Cellular Immunology, vol. 145, pp. 372–379 (1992).

Weiser, W.Y., et al., "Recombinant Human Migration Inhibitory Factor has Adjuvant Activity", Proc. Natl. Acad. Sci. USA, vol. 89, pp. 8049–8052 (1992).

Cunha, F.Q., et al., "Recombinant Migration Inhibitory Factor Induces Nitric Oxide Synthase in Murine Macrophages", The Journal of Immunology, vol. 150, No. 5, pp. 1908–1912 (1993).

Rice, G.C., et al., "Chapter 24. Macrophage Migration Inhibitory Factor (MIF): A Critical Upstream Regulator of Acute and Chronic Inflammatory Responses", Annual Reports in Medical Chemistry, vol. 33, pp. 243–252 (1998).

Donnelly, S.C., et al., "Macrophage Migration Inhibitory Factor: A Regulator of Glucocorticoid Activity with a Critical Role in Inflammatory Disease", Molecular Medicine Today, vol. 3, pp. 502–507 (1997).

Bacher, M., et al., "An Essential Regulatory Role for Macrophage Migration Inhibitory Factor in T–Cell Activation", Proc. Natl. Acad. Sci. USA, vol. 93, pp. 7849–7854 (1996).

Mikayama, T., et al., "Molecular Cloning and Functional Expression of a cDNA Encoding Glycosylation–Inhibiting Factor", Proc. Natl. Acad. Sci. USA, vol. 90, pp. 10056–10060 (1993).

Hudson, J.D., et al., "A Proinflammatory Cytokine Inhibits p53 Tumor Suppressor Activity", J. Exp. Med., vol. 190, No. 10, pp. 1375–1382 (1999).

Sakaue, S., et al., "Regulation of Macrophage Migration Inhibitory Factor (MIF) Expression by Glocose and Insulin in Adipocytes In Vitro", Molecular Medicine, vol. 5, pp. 361–371 (1999).

Chesney, J., et al., "An Essential Role for Macrophage Migration Inhibitory Factor (MIF) in Angiogenesis and the Growth of a Murine Lymphoma", Molecular Medicine, vol. 5, pp. 181–191 (1999).

Shimizu, T., et al., "High Expression of Macrophage Migration Inhibitory Factor in Human Melanoma Cells and Its Role in Tumor Cell Growth and Angiogenesis", Biochemical and Biophysical Research and Communications, vol. 264, pp. 751–758 (1999).

Rosengren, E., et al., "The Immunoregulatory Mediator Macrophage Migration Inhibitory Factor (MIF) Catalyzes a Tautomerization Reaction", Molecular Medicine, vol. 2, No. 1, pp. 143–149 (1996).

Bendrat, K., et al., "Biochemical and Mutational Investigations of the Enzymatic Activity of Macrophage Migration Inhibitory Factor", Biochemistry, vol. 36, No. 49, pp. 15356–15362 (1997).

Rosengren, E., et al., "The Macrophage Migration Inhibitory Factor MIF is a Phenylpyruvate Tautomerase", FEBS Letters, vol. 417, pp. 85–88 (1997).

Mutsunaga, J., et al., "Enzyme Activity of Macrophage Migration Inhibitory Factor Toward Oxidized Catecholamines", The Journal of Biological Chemistry, vol. 274, No. 6, pp. 3268–3271 (1999).

Lolis, E., et al., "Crystal Structure of Macrophage Migration Inhibitory Factor (MIF), a Glucocorticoid–Induced Regulator of Cytokine Production, Reveals a Unique Architecture", Proceedings of the Association of American Physicians, vol. 108, No. 6, pp. 415–419 (1996).

Swope, M., et al., "Direct Link Between Cytokine Activity and a Catalytic Site for Macrophage Migration Inhibitory Factor", The EMBO Journal, vol. 17, No. 13, pp. 3534–3541 (1998).

Sugimoto, H., et al., "Crystal Structure of Human D–Dopachrome Tautomerase, a Homologue of Macrophage Migration Inhibitory Factor, at 1.54 Å Resolution", Biochemistry, vol. 38, pp. 3268–3279 (1999).

Lubetsky, J.B., et al., "Pro–1 of Macrophage Migration Inhibitory Factor Functions as a Catalytic Base in the Phenylpyruvate Tautomerase Activity", Biochemistry, vol. 38, pp. 7346–7354 (1999).

Taylor, A.B., et al., "Crystal Structure of Macrophage Migration Inhibitory Factor Complexed with (E)–2–Fluor–p–hydroxycinnamate at 1.8 ÅResolution: Implications for Enzymatic Catalysis and Inhibition", Biochemistry, vol. 38, pp. 7444–7452 (1999).

Hermanowski–Vosatka, A., et al., "Enzymatically Inactive Macrophage Migration Inhibitory Factor Inhibits Monocyte Chemotaxis and Random Migration", Biochemistry, vol. 38, p. 12841–12949 (1999).

Stamps, S.L., et al., "Characterization of the Role of the Amino–Terminal Proline in the Enzymatic Activity Catalyzed by Macrophage Migration Inhibitory Factor", Biochemistry, vol. 37, pp. 10195–10202 (1998).

Bernhagen, J., et al., "MIF is a Pituitary–Derived Cytokine that Potentiates Lethal Endotoxaemia", Nature, vol. 365, pp. 756–759 (1993).

Kobayashi, S., et al., "Prevention of Lethal Acute Hepatic Failure by Antimacrophage Migration Inhibitory Factor Antibody in Mice Treated with Bacille Calmette–Guerine and Lipopolysaccharide", Hepatology, vol. 29, No. 6, pp. 1752–1759 (1999).

Calandra, T., et al., "Macrophage Migration Inhibitory Factor is a Critical Mediator of the Activation of Immune Cells by Exotoxins of Gram–Positive Bacteria", Proc. Natl. Acad. Sci. USA, vol. 95, pp. 11383–11388 (1998).

Makita, H., et al., "Effect of Anti–Macrophage Migration Inhibitory Factor Antibody on Lipopolysaccharide–Induced Pulmonary Neutrophil Accumulation", American Journal of Respiratory and Critical Care Medicine, vol. 158, pp. 573–579 (1998).

Kitaichi, N., et al., "Inhibition of Experimental Autoimmune Uveoretinitis with Anti–Macrophage Migration Inhibitory Factor Antibodies", Current Eye Research, vol. 20, No. 2, pp. 109–114 (2000).

Leech, M., et al., "Macrophage Migration Inhibitory Factor in Rheumatoid Arthritis", Arthritis & Rheumatism, vol. 42, No. 8, p. 1601–1608 (1999).

Abe, R., et al., "Enhancement of Macrophage Migration Inhibitory Factor (MIF) Expression in Injured Epidermis and Cultured Fibroblasts", Biochemica et Biphysica Acta, vol. 1500, pp. 1–9 (2000).

Donnelly, S.C., et al., "Regulatory Role for Macrophage Migration Inhibitory Factor in Acute Respiratory Distress Syndrome", Nature Medicine, vol. 3, No. 3, pp. 320–323 (1997).

Leech, M., et al., "Involvement of Macrophage Migration Inhibitory Factor in the Evolution of Rat Adjuvant Arthritis", Arthritis & Rheumatism, vol. 41, No. 5, pp. 910–917 (1998).

Onodera, S., et al., "High Expression of Macrophage Migration Inhibitory Factor in the Synovial Tissues of Rheumatoid Joints", Cytokine, vol. 11, No. 2, pp. 163–167 (1999).

Mikulowska, A., et al., "Macrophage Migration Inhibitory Factor is Involved in the Pathogenesis of Collagen Type II–Induced Arthritis in Mice", J. Immunol., vol. 158, pp. 5514–5517 (1997).

Shimizu, T., et al., "Identification of Macrophage Migration Inhibitory Factor (MIF) in Human Skin and its Immunohistochemical Localization", FEBS Letters, vol. 381, pp. 199–202 (1996).

Takahashi, N., et al., "Involvement of Macrophage Migration Inhibitory Factor (MIF) in the Mechanism of Tumor Cell Growth", Molecular Medicine, vol. 4, pp. 707–714 (1998).

Bozza, M., et al., "Targeted Disruption of Migration Inhibitory Factor Gene Reveals Its Critical Role in Sepsis", J. Exp. Med., vol. 189, No. 2, pp. 341–346 (1999).

Fingl, E., et al., "Chapter 1: General Principles", The Pharmacological Basis of Therapeutics, pp. 1–53 (1975).

Dahlin, D.C., et al., "Synthesis, Decomposition Kinetics, and Preliminary, Toxicological Studies of Pure Acetyl–p–benzoquinone Imine, a Proposed Toxic Metabolite of Acetaminophen", Journal of Medicinal Chemistry, vol. 25, No. 8, pp. 885–886 (1982).

Rashed, M.S., et al., "Use of Thermospray Liquid Chromatography–Mass Spectrometry for Characterization of Reactive Metabolites of 3'–Hydroxyacetanilide, a Non–Hepatotoxic Regioisomer of Acetaminophen", Journal of Chromatography, vol. 474, pp. 209–222 (1989).

Fernando, C.R., et al., "Studies on the Mechanism of Toxicity of Acetaminophen. Synthesis and Reactions of N–Acetyl–2,6–Dimethyl–and N–Acetyl–3, 5–Dimethyl–p–Benzoquinone Imines", Journal of Medicinal Chemistry, vol. 23, No. 11, pp. 1153–1158 (1980).

Holme, J.A., et al., "Comparative Cytotoxic Effects of Acetaminophen (N–Acetyl–p–Aminophenol), A Non–Hepatotoxic Regioisomer Acetyl-m–Aminophenol and Their Postulated Reactive Hydroquinone and Quinone Metabolites in Monolayer Cultures of Mouse Hepatocytes", Bicohemical Pharmacology, vol. 42, No. 5, pp. 1137–1142 (1991).

Bernhagen, J., et al., "Purification, Bioactivity, and Secondary Structure Analysis of Mouse and Humana Macrophage Migration Inhibitory Factor (MIF)", Biochemistry, vol. 33, pp. 14144–14155 (1994).

Van Schaftingen, E., et al., "A Kinetic Study of Pyrophosphate: Fructose–6–Phosphate Phosphotransferase from Potato Tubers", Eur. J. Biochem., vol. 129, pp. 191–195 (1982).

Albano, E., et al., "Mechanisms of N–Acetyl–p–Benzoquinone Imine Cytoxicity", Molecular Pharmacology, vol. 28, pp. 306–311 (1985).

Chen, W., et al., "Protein and Nonprotein Cysteinyl Thiol Modification by N–Acetyl–p–Benzoquinone Imine Via a Novel Ipso Adduct", Biochemistry, vol. 38, pp. 8159–8166 (1999).

Streeter, A.J., et al., "Cross–Linking of Protein Molecules by the Reactive Metabolite of Acetaminophen, N–Acetyl–p–Benzoquinone Imine, and Related Quinold Compounds", Exp. Med. Biol., vol. 197, pp. 727–737 (1986).

Halmes, N.C., et al., "Glutamate Dehydrogenase Covalently Binds to a Reactive Metabolite of Acetaminophen", Chem. Res. Toxicol., vol. 9, pp. 541–546 (1996).

Chen, W., et al., "Oxidation of Acetaminophen to Its Toxic Quinone Imine and Nontoxic Catechol Metabolites by Baculovirus–Expressed and Purified Human Cytochromes P450 2E1 and 2A6", Chem. Res. Toxicol., vol. 11, pp. 295–301, (1998).

Chesney, J., et al., "An Inducible Gene Product for 6–Phosphofructo–2–Kinase with an AU–Rich Instability Element: Role in Tumor Cell Glycosis and the Warburg Effect", Proc. Natl. Acad. Sci. USA, vol. 96, pp. 3047–3052 (1999).

Van Schaftingen, et al., "Control of Liver 6–Phosphofructokinase by Fructose 2,6–Bisphosphate and Other Effectors", Proc. Natl. Sci. USA, vol. 78, No. 6, pp. 3483–3486 (1981).

Yamasaki, H., et al., "TNF–$\alpha$ Stimulates Glucose Uptake in L6 Myoblasts", Diabetes Research and Clinical Practice, vol. 32, pp. 11–18 (1996).

Mitchell, R.A., et al., "Sustained Mitogen–Activated Protein Kinase (MAPK) and Cytoplasmic Phospholipase A2 Activation by Marcrophage Migration Inhibitory Factor (MIF)", The Journal of Biological Chemistry, vol. 274, No. 25, pp. 18100–18106 (1999).

Meinhardt, A., et al., "Macrophage Migration Inhibitory Factor Production by Leydig Cells: Evidence for a Role in the Regulation of Testicular Function", Endocrinology, vol. 137, No. 11, pp. 5090–5095 (1996).

* cited by examiner 1 (DOPACHROME METHYL ESTER, RED)   2 (TAUTOMERIZED PRODUCT, COLORLESS)

3 (ACETAMINOPHEN)   4 (NAPQI)   5   6

COMPOUNDS HAVING MIF ANTAGONIST ACTIVITY

TECHNICAL FIELD OF THE INVENTION

The present invention provides methods of use and pharmaceutical compositions for related genera of low molecular weight compounds comprising optionally substituted iminoquinone and orthoquinoid ring systems. The compounds have MIF (macrophage migration inhibitory factor) antagonist activity and find utility as such. For example, the MIF antagonists are useful in methods for treating a variety of diseases involving inflammatory activity or pro-inflammatory cytokine responses, such as autoimmune diseases, asthma, arthritis, EAE, ARDS (acute respiratory distress syndrome) and various forms of sepsis and septic shock, and other conditions characterized by underlying MIF responses including, for instance, tumor growth and neovascularization.

BACKGROUND OF THE INVENTION

Macrophage migration inhibitory factor (MIF) is one of the earliest described cytokines, and is an immunoregulatory protein with a wide variety of cellular and biological activities (for reviews see: Swope & Lolis, *Rev. Physiol. Biochem. Pharmacol.* 139:1–32, 1999; Metz & Bucala, *Adv. Immunol.* 66:197–223, 1997; and Bucala, *FASEB J.* 14:1607–1613, 1996). Originally, MIF was found to be secreted by activated lymphoid cells, to inhibit the random migration of macrophages, and to be associated with delayed-type hypersensitivity reactions (George & Vaughan, *Proc. Soc. Exp. Biol. Med.* 111:514–521, 1962; Weiser et al., *J. Immunol.* 126:1958–1962, 1981; Bloom & Bennett, *Science*, 153:80–82, 1966; David, *Proc. Natl. Acad. Sci. USA* 56:72–77, 1966). MIF was also shown to enhance macrophage adherence, phagocytosis and tumoricidal activity (Nathan et al., *J. Exp. Med.* 137:275–288, 1973; Nathan et al., *J. Exp. Med.* 133:1356–1376, 1971; Churchill et al., *J. Immunol.* 115:781–785, 1975). Unfortunately, many of these early studies used mixed-culture supernatants that were shown later to contain other cytokines, such as IFN-γ and IL-4 that also have macrophage migration inhibitory activity (McInnes & Rennick, *J. Exp. Med.* 167:598–611, 1988; Thurman et al., *J. Immunol.* 134:305–309, 1985) making the historical attribution of specific biological activities to the single protein now defined as MIF somewhat problematic. The availability of recombinant MIF has allowed for confirmation of these biological activities, and for the identification of additional activities.

Recombinant human MIF was originally cloned from a human T cell library (Weiser et al., *Proc. Natl. Acad. Sci. USA* 86: 7522–7526, 1989), and was shown to activate blood-derived macrophages to kill intracellular parasites and tumor cells in vitro, to stimulate IL-1γ and TNFα expression, and to induce nitric oxide synthesis (Weiser et al., *J. Immunol.* 147:2006–2011, 1991; Pozzi et al., *Cellular Immunol.* 145:372–379, 1992; Weiser et al., *Proc. Natl. Acad. Sci. USA* 89:8049–8052, 1992; Cunha et al., *J. Immunol.* 150:1908–1912, 1993). While the conclusions available from several of these early reports are confounded by the presence of a bioactive mitogenic contaminant in the recombinant MIF preparations used, the potent pro-inflammatory activities of MIF have been re-defined in other studies that do not suffer from this complicating factor (reviewed in Bucala, The FASEB Journal 10:1607–1613, 1996).

More recent MIF studies have capitalized on the production of recombinant MIF in purified form as well as the development of MIF-specific polyclonal and monoclonal antibodies to establish the biological role of MIF in a variety of normal homeostatic and pathophysiological settings (reviewed in Rice et al., *Annual Reports in Medicinal Chemistry* 33:243–252, 1998). Among the most important insights of these later reports has been the recognition that MIF not only is a cytokine product of the immune system, but also is a hormone-like product of the endocrine system, particularly the pituitary gland. This work has underscored the potent activity of MIF as a counter-regulator of the anti-inflammatory effects of the glucocorticoids (both those endogenously released and those therapeutically administered), with the effect that the normal activities of glucocorticoids to limit and suppress the severity of inflammatory responses are inhibited by MIF. The endogenous MIF response is thus seen as a cause or an exacerbative factor in a variety of inflammatory diseases and conditions (reviewed in Donnelly and Bucala, *Molecular Medicine Today* 3:502–507, 1997).

MIF is now known to have several biological functions beyond its long-hypothesized association with delayed-type hypersensitivity reactions. For example, as mentioned above, MIF released by macrophages and T cells acts as a pituitary mediator in response to physiological concentrations of glucocorticoids (Bucala, *FASEB J.* 14:1607–1613, 1996). This leads to an overriding effect of glucocoticoid immunosuppressive activity through alterations in TNF-α, IL-1β, IL-6, and IL-8 levels. Additional biological activities of MIF include the regulation of stimulated T cells (Bacher et al., *Proc. Natl. Acad. Sci. USA* 93:7849–7854, 1996), the control of IgE synthesis (Mikayama et al., *Proc. Natl. Acad. Sci. USA* 90:10056–60, 1993), the functional inactivation of the p53 tumor suppressor protein (Hudson et al., *J. Exp. Med.* 190:1375–1382, 1999), the regulation of glucose and carbohydrate metabolism (Sakaue et al., *Mol. Med.* 5:361–371, 1999), and the attenuation of tumor cell growth and tumor angiogenesis (Chesney et al., *Mol Med.* 5:181–191, 1999; Shimizu et al., *Biochem. Biophys. Res. Commun.* 264:751–758, 1999).

MIF shares significant sequence homology (36% identity) with D-dopachrome tautomerase, and MIF has enzymatic activity to catalyze the tautomerization of the non-physiological substrates D-dopachrome (Rosengren et al., *Mol. Med.* 2:143–149, 1996) and L-dopachrome methyl ester (Bendrat et al., *Biochemistry*, 36:15356–15362, 1997) (FIG. 1A). Additionally, phenylpyruvic acid and p-hydroxyphenylpyruvic acid (Rosengren et al., *FEBS Letter*, 417:85–88, 1997), and 3,4-dihydroxyphenylaminechrome and norepinephrinechrome (Matsunaga et al., *J. Biol. Chem.*, 274:3268–3271, 1999) are MIF substrates, although it is not known if tautomerization of any of these agents comprises a natural function for MIF.

The three-dimensional crystal structure of human MIF reveals that the protein exists as a homotrimer (Lolis et al., *Proc. Ass. Am. Phys.* 108:415–419, 1996) and is structurally related to 4-oxalocrotonate tautomerase, 5-(carboxymethyl)-2-hydroxymuconate isomerase, chorismate mutase, and to D-dopachrome tautomerase (Swope et al., *EMBO J.* 17:3534–3541, 1998; Sugimoto et al., *Biochemistry*, 38:3268–3279, 1999). Recently, the crystal structure has been reported for the complex formed between human MIF and p-hydroxyphenylpyruvic acid (Lubetsky et al., *Biochemistry*, 38:7346–54, 1999). It was found that the substrate binds to a hydrophobic cavity at the amino terminus and interacts with Pro-1, Lys-32, and Ile-64 in one of the subunits, and with Tyr-95 and Asn-97 in an adjacent subunit. Similar interactions between murine MIF and (E)-2-fluoro-p-hydroxycinnamate have been reported (Taylor et al., *Biochemistry*, 38:7444–7452, 1999). Solution studies using NMR provide further evidence of the interaction between p-hydroxyphenylpyruvic acid and Pro-1 in the amino-terminal hydrophobic cavity (Swope et al., *EMBO J.*, 17:3534–3541, 1998).

Mutation studies provide convincing evidence that Pro-I is involved in the catalytic function of MIF. Deletion of Pro-1 or replacement of Pro-1 with Ser (Bendrat et al., *Biochemistry*, 36:15356–15362, 1997), Gly (Swope et al., *EMBO J.*, 17:3534–3541, 1998), or Phe (Hermanowski-Vosatka et al., *Biochemistry*, 38:12841–12849, 1999), and addition of an N-terminal peptide tag to Pro-1 (Bendrat et al., *Biochemistry*, 36:15356–15362, 1997) abrogated the catalytic activity of MIF in assays using L-dopachrome methyl ester and p-hydroxyphenylpyruvic acid. A similar loss in activity was found by inserting Ala between Pro-1 and Met-2 (Lubetsky et al., *Biochemistry*, 38:7346–54, 1999), and by derivatization of Pro-1 with 3-bromopyruvate (Stamps et al., *Biochemistry* 37:10195–10202, 1998).

The connection between the enzyme and biological activities, however, remains unclear. The Pro to Ser MIF mutant showed glucocorticoid counter-regulatory activity (Bendrat et al., *Biochemistry*, 36:15356–15362, 1997) and was fully capable, as was the Pro to Phe mutant, of inhibiting monocyte chemotaxis (Hermanowski-Vosatka et al., *Biochemistry*, 38:12841–12849, 1999). In contrast, the Pro to Gly MIF mutant was greatly impaired in its activity to stimulate superoxide generation in activated neutrophils (Swope et al., *EMBO J.*, 17:3534–3541, 1998). These results suggest that specific biological activities of enzymatically inactive MIF mutants may be differentially sensitive to specific mutations, reflected in differential effects in specific assays that are used to assess biological function.

There is a need in the art to discover and develop small organic molecules that function as MIF antagonists and further posses the benefits of small organic molecule therapeutics versus larger, oligomeric protein-(e.g., antibody) and nucleic acid-based (e.g., anti-sense) therapeutic agents. The therapeutic potential of low molecular weight MIF inhibitors is substantial, given the activities of anti-MIF antibodies in models of endotoxin- and exotoxin-induced toxic shock (Bernhagen et al., *Nature*, 365:756–759, 1993; Kobayashi et al., *Hepatology*, 29:1752–1759, 1999; Calandra et al., *Proc. Natl. Acad. Sci. USA.*, 95:11383–11388, 1998; and Makita et al., *Am. J. Respir. Crit. Care Med.* 158:573–579, 1998), T-cell activation (Bacher et al., *Proc. Natl. Acad. Sci. USA.* 93:7849–7854, 1996), autoimmune diseases (e.g., graft versus host disease, insulin-dependent diabetes, and various forms of lupus) including rheumatoid arthritis (Kitaichi et al., *Curr. Eye Res.*, 20:109–114, 2000; Leech et al., *Arthritis Rheum.*, 42:1601–1608, 1999), wound healing(Abe et al., *Biochim. Biophys. Acta*, 1500:1–9, 2000), and angiogenesis (Shimizu et al., *Biochem. Biophys. Res. Commun.* 264:751–758, 1999). Low molecular weight anti-MIF antagonists (drugs) may offer clinical advantages over neutralizing antibodies and nucleic acid-based agents because the drug-like therapeutics may be orally active or generally more easily administered, have better bioavailabilities, have improved biodistributions, and should be much cheaper to produce. Prior to the present invention, the only published report of potent low molecular weight MIF inhibitors concerned some commonly found long chain fatty acids that reversibly inhibited the dopachrome tautomerase activity of mouse MIF (Bendrat et al., *Biochemistry*, 36:15356–15362, 1997). These fatty acids were never tested for their effects in biological assays of MIF activity.

SUMMARY OF THE INVENTION

The enzyme activity (tautomerase) of MIF and the substrates it accepts provide an enzymatic activity assay for designing low molecular weight agents that bind to MIF and disrupt its biological activity. The present invention provides methods of use for two related genera of such compounds having either iminoquinone-related or orthoquinoid-type structures. The iminoquinone-derived compounds are related to acetaminophen and some of its active metabolites. These agents react covalently with MIF, block its enzymatic activity, and have effects on MIF biological activity.

The present invention provides a method for treating inflammatory disorders including, but not limited to, arthritis, proliferative vascular disease, EAE, ARDS (acute respiratory distress syndrome), cytokine-mediated toxicity, sepsis, septic shock, psoriasis, interleukin-2 toxicity, asthma, MIF-mediated conditions, autoimmune disorders (including but not limited to, rheumatoid arthritis, insulin-dependent diabetes, multiple sclerosis, graft versus host disease, lupus syndromes), tumor growth or angiogenesis, or any condition characterized by local or systemic MIF release or synthesis, comprising administering an effective amount of a compound of formula I or formula II wherein formula I is:

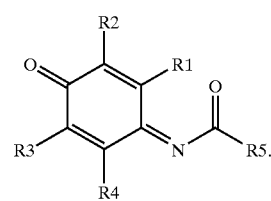

wherein $R_1$, $R_2$, $R_3$, and $R_4$ are independently H, $CH_3$, $CH_2CH_3$, OH, $OCH_3$, $OCH_2CH_3$, or halo (Br, Cl, F, or I) and $R_5$ is independently H, $CH_3$, $CH_2CH_3$, OH, $OCH_3$, $OCH_2CH_3$, or $NR_6R_7$ wherein $R_6$ and $R_7$ are independently H or $C_{1-4}$alkyl; and wherein formula II is:

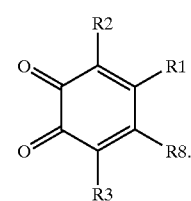

wherein $R_1$, $R_2$ and $R_3$ are independently as defined above and $R_8$ is $(CH=CH)_n$—CO—$R_5$ wherein n=0, 1, 2, or 3 and $R_5$ is independently as defined above for formula I.

Preferably for formula I: $R_5$ is $CH_3$; and $R_1$, $R_2$, $R_3$ and $R_4$ are independently H, OH, $CH_3$, $OCH_3$ or $OCH_2CH_3$. More preferably for formula I: $R_5$ is $CH_3$; $R_1$ and $R_4$ are H; and $R_2$ and $R_3$, independently are H, OH, $CH_3$, $OCH_3$ or $OCH_2CH_3$. Even more preferably for formula I: $R_5$ is $CH_3$; $R_1$, $R_2$ and $R_4$ are H; and $R_3$ is OH. Preferably for formula II: n is 1 and $R_5$ is OH; and $R_1$, $R_2$ and $R_3$, independently are H, OH, $CH_3$, $OCH_3$ or $OCH_2CH_3$. More preferably for formula II: n is 1 and $R_5$ is OH; $R_1$ is H; and $R_2$ and $R_3$, independently are H, OH, $CH_3$, $OCH_3$ or $OCH_2CH_3$. Even more preferably for formula II: n is 1 and $R_5$ is OH; and $R_1$, $R_2$ and $R_3$ are H.

The present invention further provides a pharmaceutical composition comprising a quinone-related compound, or a pharmaceutically acceptable salt thereof, and a pharmaceutically acceptable carrier or diluent, wherein the compound comprises a compound of formula I or II wherein formula I is:

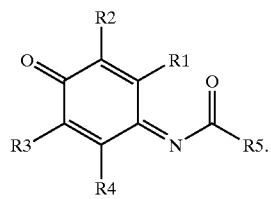

I wherein $R_1$, $R_2$, $R_3$, and $R_4$ are independently H, $CH_3$, $CH_2CH_3$, OH, $OCH_3$, $OCH_2CH_3$, or halo (Br, Cl, F, or I) and $R_5$ is independently H, $CH_3$, $CH_2CH_3$, OH, $OCH_3$, $OCH_2CH_3$, or $NR_6R_7$ wherein $R_6$ and $R_7$ are independently H or $C_{1-4}$alkyl; and wherein formula II is:

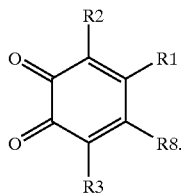

II wherein $R_1$, $R_2$ and $R_3$ are independently as defined above and $R_8$ is $(CH=CH)_n$—CO—$R_5$ wherein n=0, 1, 2, or 3 and $R_5$ is independently as defined above for formula I.

Preferably for formula I: $R_5$ is $CH_3$; and $R_1$, $R_2$, $R_3$ and $R_4$ are independently H, OH, $CH_3$, $OCH_3$ or $OCH_2CH_3$. More preferably for formula I: $R_5$ is $CH_3$; $R_1$ and $R_4$ are H; and $R_2$ and $R_3$, independently are H, OH, $CH_3$, $OCH_3$ or $OCH_2CH_3$. Even more preferably for formula I: $R_5$ is $CH_3$; $R_1$, $R_2$ and $R_4$ are H; and $R_3$ is OH. Preferably for formula II: n is 1 and $R_5$ is OH; and $R_1$, $R_2$ and $R_3$, independently are H, OH, $CH_3$, $OCH_3$ or $OCH_2CH_3$. More preferably for formula II: n is 1 and $R_5$ is OH; $R_1$ is H; and $R_2$ and $R_3$, independently are H, OH, $CH_3$, $OCH_3$ or $OCH_2CH_3$. Even more preferably for formula II: n is 1 and $R_5$ is OH; and $R_1$, $R_2$ and $R_3$ are H.

Preferably, the pharmaceutical composition further comprises a steroid, a glucocorticoid, anti-TNFα antibody, anti-IL-1 antibody, anti-IFN-γ antibody, IL-1RA, IL-10 or combinations thereof.

The present invention also provides a pharmaceutical composition comprising a quinone-related compound, and a pharmaceutically acceptable carrier, wherein the quinone-related compound forms a stable covalent interaction with an amino acid residue of a MIF protein. Preferably, the compound is a substituted iminoquinone compound or a substituted orthoquinone compound. Preferably, the pharmaceutical composition further comprises a steroid, a glucocorticoid, anti-TNFα antibody, anti-IL-1 antibody, anti-IFN-γ antibody, IL-1RA, IL-10 or combinations thereof.

The present invention provides a method for treating inflammatory disorders (including, but not limited to, arthritis, proliferative vascular disease, EAE, ARDS (acute respiratory distress syndrome), cytokine-mediated toxicity, sepsis, septic shock, psoriasis, interleukin-2 toxicity, asthma, MIF-mediated conditions, autoimmune disorders (including but not limited to, rheumatoid arthritis, insulin-dependent diabetes, multiple sclerosis, graft versus host disease, lupus syndromes), tumor growth or angiogenesis, or any condition characterized by local or systemic MIF release or synthesis, comprising administering an effective amount of a quinone-related compound, wherein the quinone-related compound forms a stable covalent interaction with an amino acid residue of a MIF protein. Preferably, the compound is a substituted iminoquinone compound or a substituted orthoquinone compound.

NIH/3T3 cells were labeled with 1 µM [$^{14}$C]-arachidonic acid. After overnight culture, the cells were washed extensively with PBS and then the appropriate samples of MIF or MIF-NAPQI (4) conjugate were added in duplicate. The release of arachidonic acid into the culture medium was then measured. These data show that unlike unmodified MIF, MIF-NAPQI (4) conjugate does not induce arachidonic acid release from NIH(3T3 cells.

Figure 7:
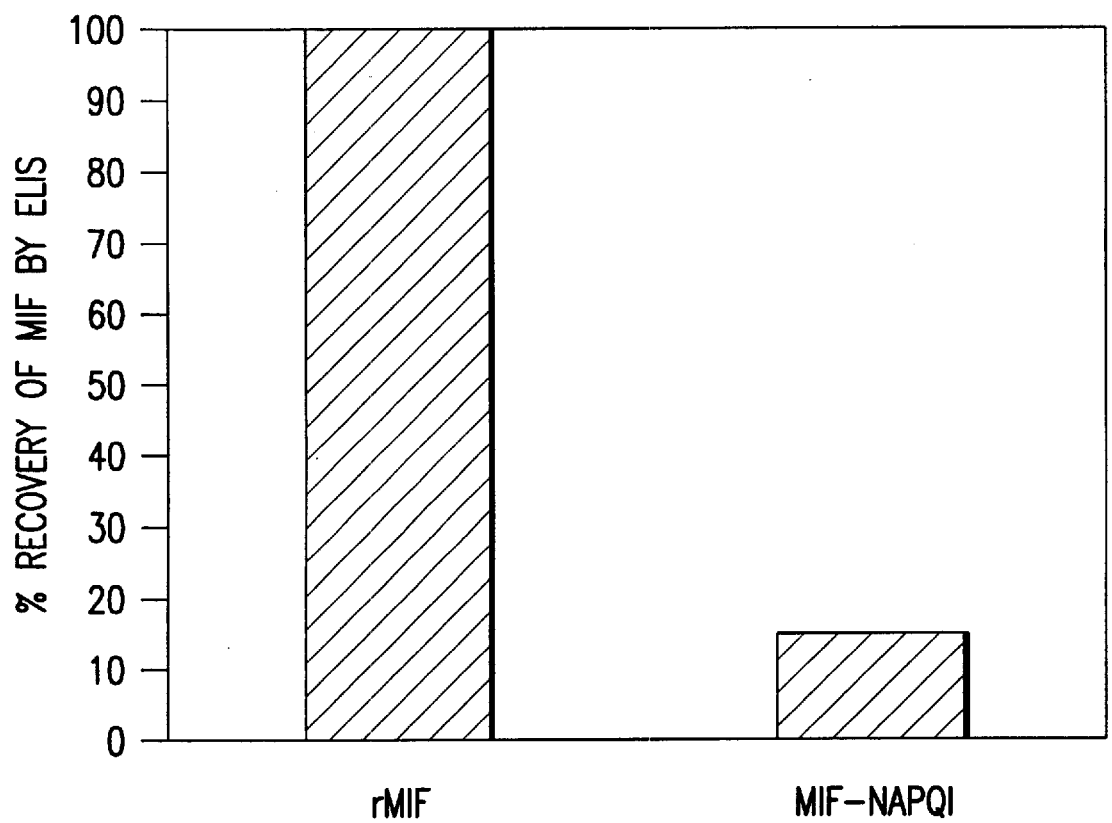

FIG. 7 illustrates the loss of immunological crossreactivity with anti-MIF antibodies following incubation of MIF with NAPQI (4). Anti-MIF antibodies bound significantly less MIF-NAPQI conjugate (resulting from incubation of NAPQI (4) at a concentration of about 5 µM-500 µM with MIF at a concentration of about 0.1 to 10 µg/ml in buffer with or without additional protein at room temperature for a period of about 0.5 to 50 min) than unmodified MIF, as assessed by a standardized ELISA for MIF.

DETAILED DESCRIPTION OF THE INVENTION

Definitions. Anti-TNFα antibody, anti-IL-1 antibody and anti-IFN-γ antibody refer to antibodies that specifically recognize one or more epitopes of TNFα, IL-1 or INF-γ, respectively, or conserved variants of TNFα, IL-1 or INF-γ, respectively, or peptide fragments of TNFα, IL-1 or INF-γ, respectively, including but not limited to polyclonal antibodies, monoclonal antibodies (mAbs), humanized or chimeric antibodies, single-chain antibodies, Fab fragments, F(ab')$_2$ fragments, fragments produced by an Fab expression library, anti-idiotypic (anti-Id) antibodies, and respective epitope-binding fragments of any of the above.

The present invention provides two related genera of MIF antagonist compounds described by formula I and formula II wherein formula I is:

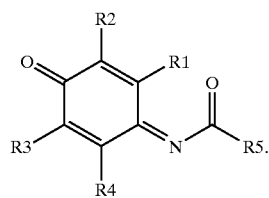

I wherein $R_1$, $R_2$, $R_3$, and $R_4$ are independently H, $CH_3$, $CH_2CH_3$, OH, $OCH_3$, $OCH_2CH_3$, or halo (Br, Cl, F, or I) and $R_5$ is independently H, $CH_3$, $CH_2CH_3$, OH, $OCH_3$, $OCH_2CH_3$, or $NR_6R_7$ wherein $R_6$ and $R_7$ are independently H or $C_{1-4}$alkyl; and wherein formula II is:

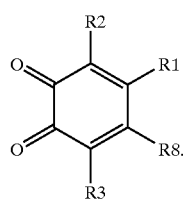

II wherein $R_1$, $R_2$ and $R_3$ are independently as defined above and $R_8$ is $(CH=CH)_n$-$CO$-$R_5$ wherein n=0, 1, 2, or 3 and $R_5$ is independently as defined above for formula I.

Preferably for formula I: $R_5$ is $CH_3$; and $R_1$, $R_2$, $R_3$ and $R_4$ are independently H, OH, $CH_3$, $OCH_3$ or $OCH_2CH_3$. More preferably for formula I: $R_5$ is $CH_3$; $R_1$ and $R_4$ are H; and $R_2$ and $R_3$, independently are H, OH, $CH_3$, $OCH_3$ or $OCH_2CH_3$. Even more preferably for formula I: $R_5$ is $CH_3$; $R_1$, $R_2$ and $R_4$ are H; and $R_3$ is OH. Preferably for formula II: n is 1 and $R_5$ is OH; and $R_1$, $R_2$ and $R_3$, independently are H, OH, $CH_3$, $OCH_3$ or $OCH_2CH_3$. More preferably for formula II: n is 1 and $R_5$ is OH; $R_1$ is H; and $R_2$ and $R_3$, independently are H, OH, $CH_3$, $OCH_3$ or $OCH_2CH_3$. Even more preferably for formula II: n is 1 and $R_5$ is OH; and $R_1$, $R_2$ and $R_3$ are H.

These genera of compounds are identified as MIF antagonists by their inhibition of MIF enzymatic activity in vitro. These compounds are thought to act by covalent derivatization of MIF, and support for this hypothesis arises from mass spectrometric characterization of MIF derivatized by treatment with the compounds and by loss of immunological cross-reactivity with anti-MIF antibodies following exposure to the compounds. Additional indicia of MIF antagonism were provided in cell-based bioassays showing that bioactivities of MIF were lost following treatment with compounds described by the above-identified formula I and formula II.

MIF catalyzes the tautomerization of a dopachrome-related MIF substrate to a colorless product. In Table I, below (describing compounds 1–18), an IC$_{50}$ value was obtained for 16 compounds in the MIF tautomerase assay. Unless specifically indicated to the contrary, references made herein to an inhibitory concentration (e.g., IC$_{50}$ or other activity index) refer to the inhibitory activity of a test compound in an MIF tautomerase assay (as further described in detail below, and in Bendrat et al., *Biochemistry* 36:15356–15362, 1997).

MIF TAUTOMERASE ACTIVITY

MIF catalyzes a tautomerization (i.e., keto-enol isomerization) reaction (Rosengren, et al., *Molecular Medicine* 2:143–149, 1996). The most active substrate identified is a non-physiological D-isomer of dopachrome. This reaction predicts therapeutic MIF antagonist agents (see pending U.S. patent application Ser. No. 08/602,929, filed Feb. 16, 1996, and U.S. Provisional patent application Ser. No. 60/162,467, filed Feb. 29, 1999, the disclosures of which are incorporated by reference herein). Inhibition of MIF tautomerase activity is predictive of inhibition of MIF biological activity.

Figure 1A:
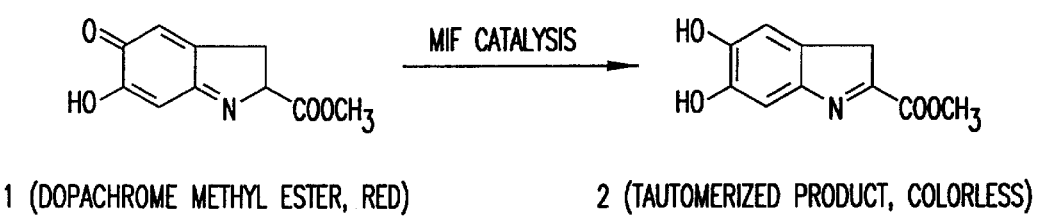
FIG. 1 shows (A) structures of dopachrome methyl ester (1), a chromogenic substrate used in enzymatic assays of MIF, and its tautomerized colorless product (2), and (B) structures of acetaminophen (3) and compounds 4–6, hepatic oxidation products thereof.
Figure 1B:
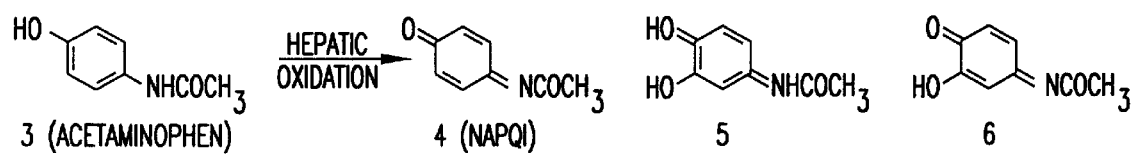

A method for performing an assay for MIF dopachrome tautomerase activity begins with the preparation and oxidation of a DOPA-related substrate precursor, such as L-3,4-dihydroxyphenylalanine methyl ester. This oxidation, for example with sodium periodate, generates the corresponding dopachrome derivative (e.g., L-3,5-dihydro-6-hydroxy-5-oxo-2H-indole-2-carboxylic acid methyl ester (1) ("dopachrome methyl ester"); see FIG. 1, compound 1), that is orange-colored and comprises a convenient substrate for use in a photometric assay for the enzymatic activity of MIF as a tautomerase. MIF (typically a purified preparation of recombinant MIF at a final concentration of 50–1000 ng/ml) addition causes the tautomerization of the colored dopachrome substrate to a colorless 5,6-dihydroxyindole-2-carboxylic acid methyl ester product (2) (FIG. 1). The enzymatic activity of MIF is measured as the rate of de-colorization of the colored solution of the dopachrome-related substrate in a suitable buffer. The absorbance is measured at about 475 nm (or 550 nm for substrate concentrations in excess 0.5 nM). A test compound may be included in the assay solution such that the effect of the test compound on MIF tautomerase activity (i.e., as an inhibitor) may be measured by noting the change in kinetics of substrate oxidation compared to control assays performed in the absence of the test inhibitor compound. In particular, the MIF tautomerase assay may be conducted essentially as follows:

L-3,4-dihydroxyphenylalanine methyl ester (e.g., Sigma D-1507) is a dopachrome substrate precursor, and is prepared as a 4 mM solution in dd $H_2O$. Sodium periodate is prepared as an 8 mM solution in dd $H_2O$. Assay Buffer (50 mM potassium phosphate/1 mM EDTA, pH 6.0) is prepared. Purified recombinant MIF is prepared in 150 mM NaCl/20 mM Tris buffer (pH 7.4) as a stock solution convenient to supply MIF at a final concentration of about 700 ng/ml. Immediately prior to initiating the assay, 3.6 ml dopachrome substrate precursor solution, 2.4 ml periodate solution and 4.0 ml Assay Buffer are combined into a homogeneous mixture (this preparation of dopachrome substrate is suitable for assay use after 1 min and for about 30 min thereafter). Test compound (typically prepared as a concentrated stock in DMSO) and MIF are then combined with 0.7 ml Assay Buffer plus 0.3 ml dopachrome substrate solution to provide the desired final concentration of the test compound in a homogeneous mixture, and the optical density (absorbance) of this assay mixture is monitored at 475 nm. Typically, $OD_{475}$ is recorded every 5 sec for 0–60 sec, and the $OD_{475}$ for a given time point is compared to parallel assays where MIF is not added or the test compound is omitted. Inhibition of MIF tautomerase activity by the test compounds is determined by inhibition of the de-colorization of the assay mixture, preferably at the 20 sec time point. $IC_{50}$ values for compounds with MIF tautomerase inhibitory activity, corresponding to the concentration of inhibitor that would inhibit MIF tautomerase activity by 50%, are determined by interpolation of the results from MIF tautomerase assays at several different inhibitor concentrations. These $IC_{50}$ values provide a reasonable correlation between MIF enzymatic inhibitory activity of the test compounds, and inhibition of the biological activity of MIF (see below).

METHODS OF TREATMENT AND PHARMACEUTICAL COMPOSITIONS

The MIF tautomerase assay was used in Examples 1 and 2 and shows that certain quinone-like compounds (optionally substituted iminoquinones and derivatized orthoquinones), inhibit MIF enzymatic activity. Furthermore, mass spectroscopy and SDS-PAGE techniques were used in Example 3 to show that such quinone-related compounds form stable covalent interactions with one or more amino acid residues of the MIF protein molecule. In other words, these quinone-like MIF antagonist compounds bind to MIF covalently. Finally, Example 4 shows that certain quinone-based compounds not only specifically inhibit MIF enzymatic activity (i.e, tautomerase), but also inhibit MIF immunoregulatory activities as measured in assays of MIF biological activity. These data provide a reasonable correlation between the MIF tautomerase enzymatic assay and MIF antagonism in a biological assay. Collectively, these data show that inhibition by a compound in the MIF tautomerase assay is predictive of its therapeutic use in inhibiting MIF biological activity.

Thus, based on the Examples of the present invention and without being bound by theory, certain quinone-based compounds can derivatize MIF covalently. Such derivatization inhibits MIF tautomerase activity and induces critical changes in the MIF protein surface, as indicated by the loss of the cross-reactivity with monoclonal anti-MIF antibodies, and the loss of MIF bioactivity in bioassays for MIF activity.

Accordingly, the present invention provides a method for inactivating enzymatic and biological activity of human MIF comprising contacting the human MIF with a quinone-related compound, or combination of compounds, that forms a stable covalent interaction with an amino acid residue of the human MIF. Preferably, the stable covalent interaction is with the N-terminal proline residue of the human MIF. Preferably, the compound is a substituted iminoquinone compound or substituted orthoquinone compound. Preferably the compound is of formula I or formula II wherein formula I is:

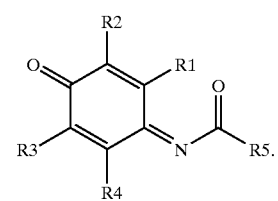

I wherein $R_1$, $R_2$, $R_3$, and $R_4$ are independently H, $CH_3$, $CH_2CH_3$, OH, $OCH_3$, $OCH_2CH_3$, or halo (Br, Cl, F, or I) and $R_5$ is independently H, $CH_3$, $CH_2CH_3$, OH, $OCH_3$, $OCH_2CH_3$, or $NR_6R_7$ wherein $R_6$ and $R_7$ are independently H or $C_{1-4}$alkyl; and wherein formula II is:

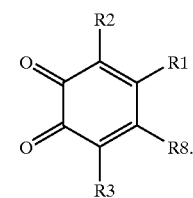

II wherein $R_1$, $R_2$ and $R_3$ are independently as defined above and $R_8$ is $(CH=CH)_n$—CO—$R_5$ wherein n=0, 1, 2, or 3 and $R_5$ is independently as defined above for formula I.

Preferably for formula I: $R_5$ is $CH_3$; and $R_1$, $R_2$, $R_3$ and $R_4$ are independently H, OH, $CH_3$, $OCH_3$ or $OCH_2CH_3$. More preferably for formula I: $R_5$ is $CH_3$; $R_1$ and $R_4$ are H; and $R_2$ and $R_3$ independently are H, OH, $CH_3$, $OCH_3$ or $OCH_2CH_3$. Even more preferably for formula I: $R_5$ is $CH_3$; $R_1$, $R_2$ and $R_4$ are H; and $R_3$ is OH. Preferably for formula II: n is 1 and $R_5$ is OH; and $R_1$, $R_2$ and $R_3$, independently are H, OH, $CH_3$, $OCH_3$ or $OCH_2CH_3$. More preferably for formula II: n is 1 and $R_5$ is OH; $R_1$ is H; and $R_2$ and $R_3$, independently are H, OH, $CH_3$, $OCH_3$ or $OCH_2CH_3$. Even more preferably for formula II: n is 1 and $R_5$ is OH; and $R_1$, $R_2$ and $R_3$ are H.

The present invention also provides a method for treating inflammatory disorders including, but not limited to, arthritis, proliferative vascular disease, EAE, ARDS (acute respiratory distress syndrome), cytokine-mediated toxicity, sepsis, septic shock, psoriasis, interleukin-2 toxicity, asthma, MIF-mediated conditions, autoimmune disorders (including, but not limited to, rheumatoid arthritis, insulin-dependent diabetes, multiple sclerosis, graft versus host disease, lupus syndromes), tumor growth or angiogenesis, or any condition characterized by local or systemic MIF release or synthesis, comprising administering an effective amount of a compound, or a combination of compounds, described by formula I or formula II.

Preferably for formula I: $R_5$ is $CH_3$; and $R_1$, $R_2$, $R_3$ and $R_4$ are independently H, OH, $CH_3$, $OCH_3$ or $OCH_2CH_3$. More preferably for formula I: $R_5$ is $CH_3$; $R_1$ and $R_4$ are H; and $R_2$ and $R_3$, independently are H, OH, $CH_3$, $OCH_3$ or $OCH_2CH_3$. Even more preferably for formula I: $R_5$ is $CH_3$; $R_1$, $R_2$ and $R_4$ are H; and $R_3$ is OH. Preferably for formula II: n is 1 and $R_5$ is OH; and $R_1$, $R_2$ and $R_3$, independently are H, OH, $CH_3$, $OCH_3$ or $OCH_2CH_3$. More preferably for formula II: n is 1 and $R_5$ is OH; $R_1$ is H; and $R_2$ and $R_3$, independently are H, OH, $CH_3$, $OCH_3$ or $OCH_2CH_3$. Even more preferably for formula II: n is 1 and $R_5$ is OH; and $R_1$, $R_2$ and $R_3$ are H.

The present invention further provides a pharmaceutical composition comprising a quinone-related compound, or a pharmaceutically acceptable salt thereof, and a pharmaceutically acceptable carrier or diluent, wherein the compound comprises a compound, or a combination of compounds, described by formula I or formula II.

Preferably for formula I: $R_5$ is $CH_3$; and $R_1$, $R_2$, $R_3$ and $R_4$ are independently H, OH, $CH_3$, $OCH_3$ or $OCH_2CH_3$. More preferably for formula I: $R_5$ is $CH_3$; $R_1$ and $R_4$ are H; and $R_2$ and $R_3$, independently are H, OH, $CH_3$, $OCH_3$ or $OCH_2CH_3$. Even more preferably for formula I: $R_5$ is $CH_3$; $R_1$, $R_2$ and $R_4$ are H; and $R_3$ is OH. Preferably for formula II: n is 1 and $R_5$ is OH; and $R_1$, $R_2$ and $R_3$, independently are H, OH, $CH_3$, $OCH_3$ or $OCH_2CH_3$. More preferably for formula II: n is 1 and $R_5$ is OH; $R_1$ is H; and $R_2$ and $R_3$, independently are H, OH, $CH_3$, $OCH_3$ or $OCH_2CH_3$. Even more preferably for formula II: n is 1 and $R_5$ is OH; and $R_1$, $R_2$ and $R_3$ are H.

The present invention also provides a pharmaceutical composition comprising a quinone-related compound, or a pharmaceutically acceptable salt thereof, and a pharmaceutically acceptable carrier or diluent, wherein the quinone-related compound forms a stable covalent interaction with an amino acid residue of a MIF protein. Preferably, the compound is a substituted iminoquinone compound or a substituted orthoquinone compound. Preferably, the compound is a substituted iminoquinone compound. Preferably, the compound comprises a compound described by the above-identified formula I or formula II.

The present invention further provides a method for treating inflammatory disorders including, but not limited to, arthritis, proliferative vascular disease, EAE, ARDS (acute respiratory distress syndrome), cytokine-mediated toxicity, sepsis, septic shock, psoriasis, interleukin-2 toxicity, asthma, MIF-mediated conditions, autoimmune disorders (including, but not limited to, rheumatoid arthritis, insulin-dependent diabetes, multiple sclerosis, graft versus host disease, lupus syndromes), tumor growth or angiogenesis, or any condition characterized by local or systemic MIF release or synthesis, comprising administering an effective amount of a quinone-related compound, or a pharmaceutically acceptable salt thereof, and a pharmaceutically acceptable carrier, wherein the quinone-related compound forms a stable covalent interaction with an amino acid residue of a MIF protein. Preferably, the compound is a substituted iminoquinone compound or a substituted orthoquinone compound. Preferably, the compound comprises a compound described by the above-identified formula I or formula II.

As an example of the methods of treatment of the present invention, quinone-like compounds of the present invention can be used to treat patients with ARDS (acute respiratory distress syndrome). ARDS is often considered to be an archetypal clinical response in which the dynamic balance within the immune response shifts toward excessive inflammation and tissue destruction. MIF is expressed in both type II alveolar cells and infiltrating immune cells. MIF levels in the bronchoalveolar lavage of ARDS patients were found to be significantly elevated when compared to control subjects (Donnelly et al., *Nat. Med.*, 3:320–323, 1997). Human MIF enhances both TNFα and IL-8 secretion from ARDS alveolar macrophages (ex vivo) when compared to control cells. Pre-treatment of these cells with anti-MIF antibodies significantly decreases TNFα and IL-8 production from ARDS alveolar cells. Moreover, as discussed above under "Background of the Invention," rMIF (recombinant MIF) was found to override, in a concentration-dependent fashion, glucocorticoid-mediated inhibition of cytokine secretion in ARDS macrophages. These were the first data to indicate that the MIF/glucocorticoid dyad is active in cells that had undergone pro-inflammatory activation in vivo during human disease (Donnelly et al., *Nat. Med.*, 3:320–323, 1997). Significantly elevated levels of alveolar MIF were found in those at-risk patients who progressed to ARDS compared to those who did not. MIF likely acts as an important mediator to promote and sustain the pulmonary inflammatory response in ARDS. Its prominent expression in ARDS may explain the fulminant course of this disease and perhaps why glucocorticoid treatment has proven disappointing in established cases. Thus, pharmaceutical compositions comprising the quinone-like compounds of the present invention can be used to treat ARDS patients, as a prototype inflammatory indication.

As a further example of the methods of treatment of the present invention, quinone-like compounds of the present invention can be used to treat patients with rheumatoid arthritis. Synovial fluid obtained from the affected joints of patients with rheumatoid arthritis contain significantly greater levels of MIF than those obtained from patients with osteoarthritis or from normal control subjects (Metz & Bucala, *Adv. Immunol.*, 66:197–223, 1997; Leech et al., *Arthritis Rheum.*, 41:910–917, 1998; Onodera et al., *Cytokine*, 11:163–167, 1999). As revealed by immunohistochemical staining methods, infiltrating mononuclear cells within the human arthritic joint are the primary source of MIF. In two animal models of arthritis, neutralizing anti-MIF mAb's significantly inhibited disease progression and disease severity (Leech et al., *Arthritis Rheum.*, 41:910–917, 1998; Mikulowska et al., *J. Immunol.*, 158:5514–5517, 1997) giving impetus to the desirability of developing additional MIF inhibitors for potential therapeutic use in inflammatory disease. Thus, pharmaceutical compositions comprising quinone-like compounds of the present invention can be used to treat arthritis patients.

In yet a further example of the methods of treatment of the present invention, quinone-like compounds of the present invention can be used to treat patients with atopic dermatits. Atopic dermatitis is a chronic pruritic inflammatory skin disorder. Its pathogenesis, in part, is thought to be due to dysregulated cytokine production by peripheral mononuclear cells. In lesions from patients with atopic dermatitis, MIF protein is diffusely distributed throughout the entire epidermal layer with increased expression by keratinocytes (Shimizu et al., *FEBS Lett.*, 381:199–202, 1996). In normal human skin, MIF has primarily been localized to epidermal ketatinocytes. The serum MIF level of atopic dermatitis patients were 6-fold higher than in control subjects. Additionally, serum MIF levels in atopic dermatitis patients decreased as clinical features improved, suggesting that MIF plays a pivotal role in the inflammatory response in the skin during dermatitis. Thus, pharmaceutical compositions comprising quinone-like compounds of the present invention can be used to treat patients with atopic dermatitis.

In a similar manner, the present invention also provides a method for treating or preventing other inflammatory or autoimmune disorders including, but not limited to, proliferative vascular disease, cytokine-mediated toxicity, sepsis, septic shock, psoriasis, interleukin-2 toxicity, asthma, MIF-mediated conditions, insulin-dependent diabetes, multiple sclerosis, graft versus host disease, lupus syndromes, EAE, and other conditions characterized by local or systemic MIF release or synthesis.

In another example of the methods of treatment of the present invention, the quinone-like compounds of the present invention can be used to treat patients with tumor growth. Neutralizing anti-MIF antibodies have been found to significantly reduce growth and vascularization (angiogenesis) of mouse 38C13 B cell lymphoma in vivo (Chesney et al., *Mol. Med.*, 5:181–191, 1999). MIF was expressed predominantly in tumor-associated neovasculature. Cultured microvascular endothelial cells, but not 38C13 B cells, were observed both to produce MIF and to require its activity for proliferation in vitro (Takahashi et al., *Mol. Med.*, 4:707–714, 1998). In addition, the administration of anti-MIF antibodies to mice was found to significantly inhibit the neovascularization response elicited by Matrigel implantation, a model of new blood vessel formation in vivo (Bozza et al., *J. Exp. Med.*, 189:341–346, 1999). These data indicate that MIF plays an important role in tumor angiogenesis, a new target for the development of anti-neoplastic agents that inhibit tumor neovascularization.

Thus, the present invention also provides a method for treating or preventing tumor growth or angiogenesis, comprising administering an effective amount of a quinone-like compound, or combination of quinone-like compounds, that forms a stable covalent interaction with an amino acid residue of a MIF protein. Preferably, the compound is a substituted iminoquinone compound or a substituted ortho-quinone compound. Preferably, the compound comprises a compound described by the above-identified formula I or formula II.

The present invention also provides a compound of formula I, or a pharmaceutically acceptable salt thereof, as a pharmaceutical composition comprising either of the aforesaid, for use in a medicine or for the manufacture of a medicament for the treatment or prevention of inflammatory disorders including arthritis, proliferative vascular disease, EAE, ARDS, cytokine-mediated toxicity, sepsis, septic shock, psoriasis, interleukin-2 toxicity, asthma, MIF-mediated conditions, autoimmune disorders (including, but not limited to, rheumatoid arthritis, insulin-dependent diabetes, multiple sclerosis, graft versus host disease, lupus syndromes), tumor growth or angiogenesis, or any condition characterized by local or systemic MIF release or synthesis.

The present invention also provides a compound of formula II, or a pharmaceutically acceptable salt thereof, as a pharmaceutical composition comprising either of the aforesaid, for use in a medicine or for the manufacture of a medicament for the treatment or prevention of inflammatory disorders including arthritis, proliferative vascular disease, ARDS, cytokine-mediated toxicity, sepsis, septic shock, psoriasis, interleukin-2 toxicity, asthma, MIF-mediated conditions, autoimmune disorders (including, but not limited to, rheumatoid arthritis, insulin-dependent diabetes, multiple sclerosis, graft versus host disease, lupus syndromes), tumor growth or angiogenesis, or any condition characterized by local or systemic MIF release or synthesis.

Combination treatment methods and compositions. In yet another embodiment, the quinone-like compounds of the present invention can be used in combination with other therapeutic agents, e.g., steroids, glucocorticoids, inhibitors of other inflammatory cytokines (e.g., anti-TNFα antibodies, anti-IL-1 antibodies, anti-IFN-γ antibodies), or with other cytokines such as IL-1RA or IL-10 (see U.S. Pat. No. 6,030,615, incorporated by reference herein in its entirety; claiming the use of anti-MIF antibody in combination with anti-TNFα, anti-IL-1, anti-IFN-γ, IL-1RA, a steroid, a glucocorticoid or IL-10 to treat cytokine-mediated toxicity).

For example, various anti-inflammatory steroids are known to induce MIF (a mediator of inflammation) secretion/release by macrophages and pituitary cells, and may thus reduce the benefit of current anti-inflammatory steroid therapy (U.S. Pat. No. 6,030,615, incorporated by reference herein in its entirety). Additionally, some steroid derivatives (e.g., 20α dihydrocortisol, a glucocorticoid) actually inhibit steroid-induced MIF release (U.S. Pat. No. 6,030,615, incorporated by reference herein in its entirety). Accordingly, the quinone-like compounds of the present invention may be used in conjunction with, e.g., steroids for the treatment or prevention of inflammatory disorders including arthritis, proliferative vascular disease, EAE, ARDS, cytokine-mediated toxicity, sepsis, septic shock, psoriasis, interleukin-2 toxicity, asthma, MIF-mediated conditions, autoimmune disorders (including, but not limited to, rheumatoid arthritis, insulin-dependent diabetes, multiple sclerosis, graft versus host disease, lupus syndromes), tumor growth or angiogenesis, or any condition characterized by local or systemic MIF release or synthesis. Such combination therapy can be designed to inhibit MIF release and/or activity locally and/or systemically.

Therefore, the present invention further provides a pharmaceutical composition comprising (a) a quinone-related compound, or a pharmaceutically acceptable salt thereof, wherein the compound comprises a compound described by the above-identified formula I or formula II, in combination with (b) steroids, glucocorticoids, anti-TNFα antibodies, anti-IL-1 antibodies, anti-IFN-γ antibodies, IL-1RA, IL-10 or combinations thereof, and a pharmaceutically acceptable carrier or diluant.

Preferably for formula I: $R_5$ is $CH_3$; and $R_1$, $R_2$, $R_3$ and $R_4$ are independently H, OH, $CH_3$, $OCH_3$ or $OCH_2CH_3$. More preferably for formula I: $R_5$ is $CH_3$; $R_1$ and $R_4$ are H; and $R_2$ and $R_3$ independently are H, OH, $CH_3$, $OCH_3$ or $OCH_2CH_3$. Even more preferably for formula I: $R_5$ is $CH_3$; $R_1$, $R_2$ and $R_4$ are H; and $R_3$ is OH. Preferably for formula II: n is 1 and $R_5$ is OH; and $R_1$, $R_2$ and $R_3$, independently are H, OH, $CH_3$, $OCH_3$ or $OCH_2CH_3$. More preferably for formula II: n is 1 and $R_5$ is OH; $R_1$ is H; and $R_2$ and $R_3$, independently are H, OH, $CH_3$, $OCH_3$ or $OCH_2CH_3$. Even more preferably for formula II: n is 1 and $R_5$ is OH; and $R_1$, $R_2$ and $R_3$ are H.

PHARMACEUTICAL FORMULATIONS

The compounds of the present invention have utility in pharmacological compositions for the treatment and prevention of many diseases and disorders characterized by an MIF response, where MIF is released from cellular sources and MIF production is enhanced. A compound of the invention can be administered to a human patient by itself or in pharmaceutical compositions where it is mixed with suitable carriers or excipients at doses to treat or ameliorate various conditions characterized by MIF release. A therapeutically effective dose further refers to that amount of the compound sufficient to inhibit MIF tautomerase activity and MIF bioactivity, it being understood that such inhibition may occur at different concentrations such that a person skilled in the art could determine the required dosage of compound to inhibit the target MIF activity. Therapeutically effective doses may be administered alone or as adjunctive therapy in combination with other treatments for inflammation, tumor growth, or associated diseases. Techniques for the formulation and administration of the compounds of the instant application may be found in "Remington's Pharmaceutical Sciences" Mack Publishing Co., Easton, Pa., latest addition.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation.

Furthermore, one may administer a compound of the present invention in a drug delivery system, for example in a liposome.

The pharmaceutical compositions and compounds of the present invention may be manufactured in a manner that is itself known, e.g., by means of conventional mixing, dissolving, dragee-making, levitating, emulsifying, encapsulating, entrapping, or lyophilizing processes. Pharmaceutical compositions for use in accordance with the present invention thus may be formulated in conventional manner using one or more physiologically acceptable carriers comprising excipients and auxiliaries that facilitate processing of the active compounds into preparations, which can be used pharmaceutically. Proper formulation is dependent upon the route of administration chosen.

For injection, the compounds of the invention may be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are known in the art.

For oral administration, the compounds can be formulated readily by combining the active compounds with pharmaceutically acceptable carriers well known to those in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the compound with a solid excipient, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared in DMSO or as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various forms of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention identified as inhibitors of MIF activity may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Salts tend to be more soluble in aqueous or other protonic solvents than are the corresponding free base forms. Examples of pharmaceutically acceptable salts, carriers or excipients are well known to those skilled in the art and can be found, for example, in *Remington's Pharmaceutical Sciences*, 18th Edition, A. R. Gennaro, Ed., Mack Publishing Co., Easton, Pa., 1990. Such salts include, but are not limited to, sodium, potassium, lithium, calcium, magnesium, iron, zinc, hydrochloride, hydrobromide, hydroiodide, acetate, citrate, tartrate and malate salts, and the like.

Pharmaceutical compositions suitable for use in the present invention include compositions wherein the active ingredients are contained in an effective amount to achieve their intended purpose. More specifically, a therapeutically effective amount means an amount effective to prevent or inhibit development or progression of a disease characterized by MIF release and production in the subject being treated. Determination of the effective amounts is well within the capability of those skilled in the art, especially in light of the detailed disclosure provided herein.

For any compound used in the method of the invention, the therapeutically effective dose can be estimated initially from tautomerase inhibition assays and cell culture assays. Such information can be used to more accurately determine useful doses in humans.

A therapeutically effective dose refers to that amount of the compound that results in a reduction in the development or severity of a disease characterized by MIF release and production. Toxicity and therapeutic efficacy of such compounds can be determined by standard pharmaceutical, pharmacological, and toxicological procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from cell culture assays or animal studies can be used in formulating a range of dosage for use in humans. The dosage of such compounds lies preferably within a range of circulating concentrations that include the $ED_{50}$ (or the $ED_{99}$) with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "*The Pharmacological Basis of Therapeutics*", Ch. 1 p. 1).

Dosage amount and interval may be adjusted individually to provide plasma levels of the active moiety which are sufficient to maintain the desired modulating effects, or minimal effective concentration (MEC). The MEC will vary for each compound but can be estimated from in vitro data; e.g., the concentration necessary to achieve a 50–97% inhibition of MIF activity. Dosages necessary to achieve the MEC will depend on individual characteristics and route of administration. However, HPLC assays, bioassays or immunoassays can be used to determine plasma concentrations.

Dosage intervals can also be determined using the MEC value. Compounds should be administered using a regimen that maintains plasma levels above the MEC for 10–90% of the time, preferably between 30–90% and most preferably between 50–90%.

In cases of local administration for instance, direct introduction into a target organ or tissue, or selective uptake, may cause the effective local concentration of the drug to be unrelated to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

MATERIALS AND METHODS

Synthesis. In the examples of the syntheses that follow, all reagents and solvents used were purchased at the highest commercial quality. All solvents used were HPLC grade from Fisher. $^1$H (270 MHz) and $^{13}$CNMR (67.5 MHz) NMR spectra were recorded on a JEOL Eclipse 270 spectrometer. Coupling constants were reported in Hertz (Hz), and chemical shifts were reported in parts per million (ppm) relative to tetramethylsilane (TMS, 0.0 ppm) with $CDCl_3$, DMSO or $CD_3OD$ as solvent. Thin layer (TLC) and flash column chromatography were performed using Alumina B, F-254 TLC plates form Selecto Scientific and Fisher Scientific Basic alumina Brockman activity I, respectively. The reactions were monitored by TLC and $^1$HNMR and were stopped when the yield of the crude according to $^1$HNMR was 90–95%.

Reagents. Unless otherwise indicated, all chemicals, including compounds 3, 12, 13, 15, 17, and 18 were purchased from Aldrich or Sigma Chemical Companies, and were of the highest grade commercially available. Compounds 4 (Dahlin & Nelson, *J. Med. Chem.*, 25:885–886, 1982), 5 (Rashed & Nelson, *J. Chromatogr.*, 474:209–222, 1988), 8, 9 (Fernando et al., *J. Med. Chem.*, 23:1153–1158, 1980), and 10 (Holme et al., *Biochem. Pharmacol.* 42:1137–1142, 1991) were prepared according to known methods. For example, NAPQI (4) was synthetically prepared from a solution of acetaminophen (1 g) in 50 ml of dry chloroform, treated with freshly prepared silver oxide. This reaction was monitored by thin layer chromatography (TLC) (diethyl ether as a mobile phase). After one hour the reaction was filtered through Celite into a flask containing 5 mg of butylated hydroxytoluene. The volume of the solution was reduced and the concentrated solution was loaded onto a dry silica gel column. The product was eluted by flash chromatography with diethyl ether. A yellow band was collected and concentrated in an ice-cooled flask using an aspirator. The remaining ether was removed under high vacuum. To obtain pure material (essential for biochemical work), sublimation of pure NAPQI (4) using a cold finger and high vaccum (0.01 mm Hg) at 20° C. was the ultimate choice. Overall yield was very low, approximately 0.5%. NAPQI (4) is dissolved in dry DMSO at a concentration of 50 mM. Small aliquots (generally 25 µL) were aliquotted into Eppendorf tubes and were stored at −70° C. When needed, the contents were quickly thawed, and unused material remaining from thawed lots was discarded. Storage in a −20° C. frost-free freezer is inadvisable, since solutions turn bright yellow within a few weeks.

Dopachrome methyl ester (1) was prepared similarly to previously published procedures (Bendrat et al., *Biochemistry*, 36:15356–15362, 1997; Swope et al., *EMBO J.*, 17:3534–3541. 1998). Briefly, to an aqueous 4 mM solution of L-3,4-dihydroxyphenylalanine methyl ester was added $NaIO_4$ to a final concentration of 6 mM. The solution was immediately placed on ice. Assays were initiated at a time when the absorbance at 475 nm reached a maximal value, signifying that the limiting reagent, $NaIO_4$, was consumed. Recombinant human and mouse MIF was expressed in *E. coli* and purified as previously reported (Bernhagan et al., *Biochemistry*, 33:14144–14155, 1994).

Compounds 6, 11, 14, and 16 were prepared from their corresponding dihydroquinones (20 mM in DMSO) through the addition of 1 volume of $NaIO_4$ at 18 mM in $H_2O$ (0.9 equivalents) at 4° C. After 5 minutes, the samples were diluted in 50% aqueous DMSO at 4° C., and were then added to recombinant mouse or human MIF at the concentrations indicated.

Treatment of MIF with Inhibitors. MIF samples (procedure A: 0.72 µg/ml in 50 mM sodium phosphate (pH 6.6) containing 20 µg/ml bovine serum albumin; procedure B: 0.72 µg/ml in 50 mM sodium phosphate (pH 6.6) containing fetal bovine serum; procedure C: 0.1–0.6 mg/ml in 50 mM sodium phosphate at pH 6.6) were treated with various concentrations of the inhibitors for 5–20 minutes (exact times are specified in the text of the Examples below) at room temperature. The modified proteins were then analyzed for enzyme activity using the dopachrome tautomerase assay. Protein concentrations were determined using the micro BCA assay (Pierce Chemical Co.).

Dopachrome Tautomerase Assays. Compound 1 (0.3 ml at 4 mM, prepared in situ) was added to a room temperature solution (0.7 ml) of recombinant mouse or human MIF (0.72 µg/ml in the specified buffers from procedures A, B, and C above). The MIF sample was immediately monitored for loss in absorbance at 475 nm compared to untreated MIF solutions and to compound 1 without the addition of MIF.

MALDI MS Experiments. Samples were run using a Perceptive Voyager DE MALDI MS (DHB matrix) at the University of Washington Department of Biochemistry Mass Spectrometry Laboratory.

Fructose-2,6-bisphosphate Assay. L6 rat myoblasts were obtained from ATCC (CRL-1458). The cells were cultured in DMEM containing 10% fetal bovine serum and were plated at 20,000 cells/ml. Differentiation was enhanced by treatment with bovine insulin (0.3 µM, Gibco) in DMEM containing 1% horse serum. After three days of incubation at 37° C., the cells were washed and complete DMEM was added. The cells were then stimulated with MIF samples (10 ng/ml), and incubation at 37° C. was continued for 24 h. After washing with serum-free medium, the cells were disrupted by adding 0.8 ml of 50 mM NaOH. Fructose-2,6-diphosphate was extracted and measured according to a known method (Van Schaftingen et al., *Eur. J. Biochem.* 129:191–195, 1982).

EXAMPLE 1

Enzyme Inhibition Studies. This example illustrates the inhibition of the enzymatic activity of human MIF by iminoquinones. The enzymatic tautomerization activity of recombinant human MIF was performed using L-dopachrome methyl ester (1) as a chromogenic substrate (Bendrat et al., *Biochemistry*, 36:15356–15362, 1997). The tautomerization reaction catalyzed by MIF, as described in detail above, leads to the formation of a dihydroxyindole product (2), which is colorless (see FIG. 1A). N-Acetyl-p-benzoquinone imine (NAPQI; 4), which possesses the iminoquinone functionality of L-dopachrome methyl ester (1) acts as a potent electrophile, and has been shown to alkylate glutathione (Albano et al., *Mol. Pharmacol.*, 28:306–311, 1985), and proteins such as papain (Chen et al., *Biochemistry*, 38:8159–8166, 1999), BSA (Streeter et al., *Exp Med Biol.*, 197:727–737, 1986), and glutamate dehydrogenase (Halmes et al., *Chem. Res. Toxicol.* 9:541–546, 1996).

Figure 2:
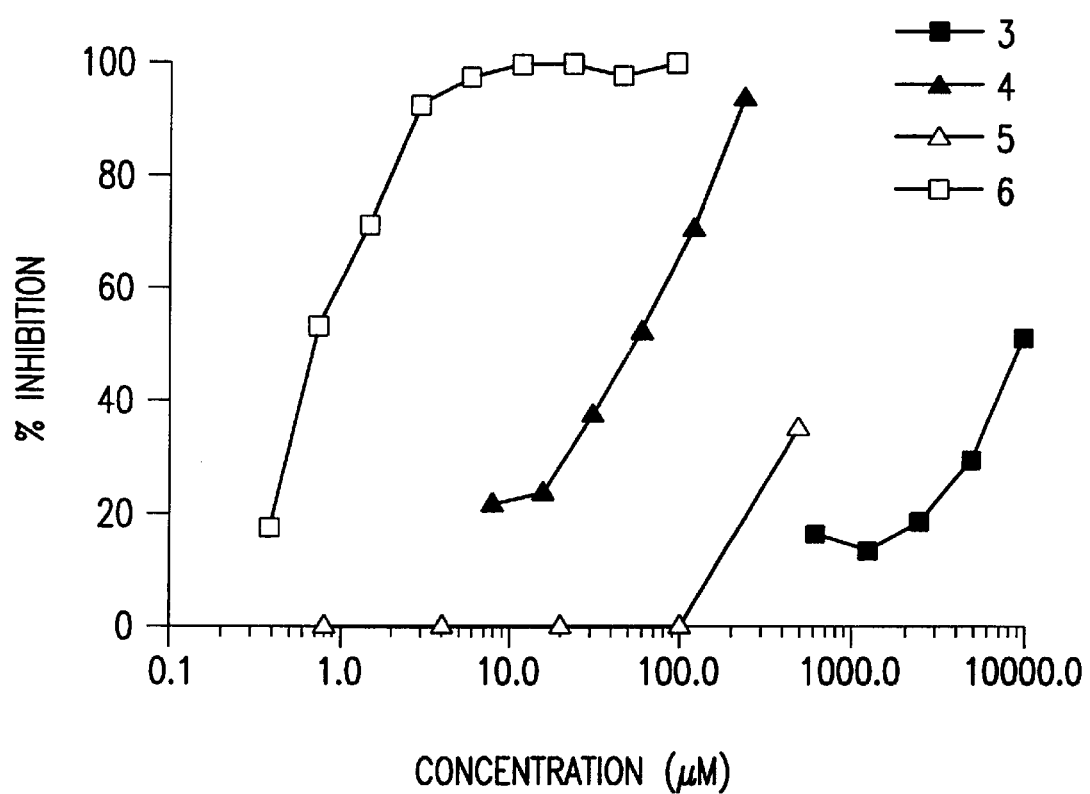
FIG. 2 shows the inhibition of the enzymatic activity of recombinant human MIF by acetaminophen (3) and some of its metabolites (4–6). MIF (0.72 μg/mL) was treated with various concentrations of the inhibitors for 5 minutes, and the effects on tautomerase enzymatic activity compared to untreated controls were determined using dopachrome methyl ester (1) as a substrate. NAPQI (4) is a potent inhibitor.

Compound 4 was tested to determine if it would bind to the enzyme active site of MIF, and potentially form a covalent adduct. Enzyme inhibition assays were performed by treating MIF with various concentrations of compounds 3–6 for 5 minutes, adding dopachrome methyl ester 1, and measuring the rate of conversion of compound 1 to compound 2 compared to untreated MIF. Acetaminophen (3) was very weakly inhibitory, and had an $IC_{50}$ value of 10 mM (see FIG. 2). NAPQI (4), the well-characterized hepatic oxidation product of acetaminophen (Dahlin & Nelson, *J. Med. Chem.*, 25:885–886, 1982; Chen et al., *Chem. Res. Toxicol.* 11:295–301, 1998), was significantly more potent, with an $IC_{50}$ value of 40 µM, 250 times lower than that of compound 3. The most potent compound in this series was the derivatized hydroxyiminoquinone 6, which had an $IC_{50}$ value of 0.7 µM. This was more than 715-fold more potent than the related dihydroquinone-like analog 5, also a known acetaminophen metabolite (Chen et al., *Chem. Res. Toxicol.* 11: 295–301, 1998).

Thus, the substituted iminoquinones 4 and 6 of the present invention are potent inhibitors of the MIF tautomerase enzymatic activity.

EXAMPLE 2

Quinone-Based Enzyme Inhibitors. This example shows the inhibitory activity of quinone-based (and iminoquinone-based) compounds against MIF enzymatic activity (summarized in Table I). The inhibitory activity of several related quinone-based compounds was tested against the enzymatic activity of MIF because compound 4, and related quinone-like agents, are known to react with nucleophiles, including thiols (Dahlin & Nelson, *J. Med. Chem.*, 25:885–886, 1982; Rashed & Nelson. *J. Chromatogr.*, 474:209–222, 1988; Fernando et al., *J. Med. Chem.*, 23:1153–1158, 1980; Holme et al., *Biochem. Pharmacol.* 42:1137–1142, 1991; Chen et al., *Chem. Res. Toxicol.* 11:295–301, 1998; Albano et al., *Mol. Pharmacol.*, 28:306–311, 1985; Chen et al., *Biochemistry*, 38:8159–8166, 1999; Streeter et al., *Adv Exp Med Biol.*, 197:727–737, 1986; and Halmes et al., *Chem. Res. Toxicol.* 9:541–546, 1996). Of approximately 60 compounds tested, the most active contained ortho and para-quinoid structures related to that found in the chromogenic substrate 1 (see Table 1). The most potent agents were the quinone-based compounds 6 and 16, which had sub-micromolar activities. Dihydroquinones containing 3,4-disubstituted benzene derivatives, such compounds 5, 10, 12, 13, and 15 possessed little, if any, MIF enzyme inhibition activity. No inhibitory activity was observed with the thiol-reactive agents, iodoacetamide (17) and N-ethylmaleimide (18), suggesting that the quinone-based inhibitors may be reacting at sites other than the free cysteines present in MIF (there are three free cysteines; Bucala, *FASEB J.* 14:1607–1613, 1996).

The efficiency of MIF enzymatic inhibition with a given inhibitor varied according to the MIF concentration in the reaction. When the reactions were performed at higher MIF concentrations (approximately 0.1 mg/ml and above), compounds 6 and 16 virtually eliminated MIF enzymatic activity at doses that were equimolar to MIF monomer. For example, when MIF at 2.8 $\mu$M (0.1 mg/ml, 8.4 $\mu$M in terms of monomer) was treated with compound 6 at 7 $\mu$M (0.83 equivalents based on monomer), 93% of the enzyme activity was lost. All of the enzyme activity was lost when the protein was treated with 1.7 equivalents/monomer. Under these reaction conditions, the inhibitory activity of compound 6 was exceedingly efficient.

Figure 3:
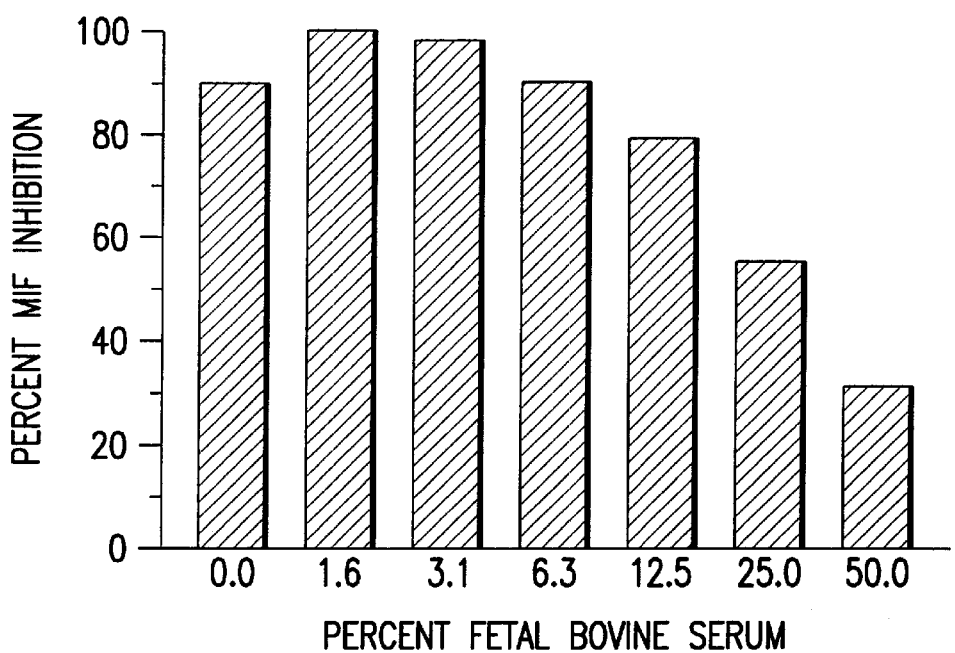
FIG. 3 shows inhibition of the enzymatic activity of recombinant human MIF by compound 4 in the presence of serum proteins. MIF was diluted (0.72 μg/mL final concentration) into solutions containing fetal bovine serum, and compound 4 (50 mM in DMSO) was added to a final concentration of 0.2 mM. Enzyme activity was determined after 20 minutes, using dopachrome methyl ester (1) as a substrate compared to identical control solutions not containing MIF. Inhibition of MIF by NAPQI occurred even in the presence of serum proteins, an indication of specificity.

Additionally, the interaction of MIF with quinone-based compounds was consistent with a specific recognition process. Insight into the specificity of enzyme inhibition by compound 4 was gained by performing inhibition assays with dilute solutions of MIF (0.72 $\mu$g/ml), and in the presence of fetal bovine serum. Only when the concentration of fetal bovine serum reached 25% was there any detectable loss in the inhibitory activity of compound 4 (see FIG. 3). There was 31% residual inhibitory activity when the serum concentration was 50%. Thus, in the presence of a huge excess (approximately 56,000-fold) of non-target protein, compound 4 still exerted significant MIF enzymatic inhibitory activity. These results indicated that quinone-based MIF inhibitors bind to the protein through a specific recognition process.

Thus, according to the present invention, the electrophilic quinone-based compounds related in structure to 1 comprise a new and general class of low molecular weight, specific inhibitors of MIF enzymatic activity.

TABLE I

Representative Compounds Tested as Inhibitors of the Enzyme Activity of MIF[a]

| Compound | Structure | $IC_{50}$ |
|---|---|---|
| 3 | HO–C6H4–NHCOCH3 | 10 mM |
| 4 | O=C6H4=N–COCH3 | 40 $\mu$M |
| 5 | (HO)2–C6H3–NHCOCH3 | 500 $\mu$M |
| 6 | O=C6H3(OH)=N–COCH3 | 0.7 $\mu$M |
| 7 | O=C6H3(CH3)=N–COCH3 | 35 $\mu$M |
| 8 | O=C6H2(CH3)2=N–COCH3 | 120 $\mu$M |
| 9 | O=C6H2(CH3)2=N–COCH3 | 200 $\mu$M |
| 10 | HO–C6H3(OMe)–NHCOCH3 | 0% inhibition at 200 $\mu$M |
| 11 | O=C6H3(OMe)=N–COCH3 | 25 $\mu$M |
| 12 | MeO–C6H3(OMe)–NHCOCH3 | 0% inhibition at 200 $\mu$M |
| 13 | (HO)2–C6H3–COOH | 24% inhibition at 200 $\mu$M |
| 14 | O=C6H3=O with COOH | 4 $\mu$M |

TABLE I-continued

Representative Compounds Tested as Inhibitors of the Enzyme Activity of MIF[a]

| Compound | Structure | IC$_{50}$ |
|---|---|---|
| 15 | 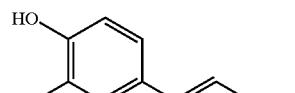 | 42% inhibition at 200 μM |
| 16 | 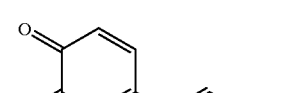 | 0.3 μM |
| 17 | 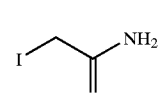 | 0% inhibition at 500 μM |
| 18 | 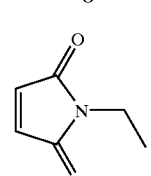 | 0% inhibition at 500 μM |

[a]MIF (0.7 μg/ml) was treated with various concentrations of the compounds for 5 minutes, and residual enzyme activity was determined using dopachrome methyl ester (1) as a substrate. IC$_{50}$ values (50% MIF inhibition) were determined based on the activities of untreated MIF.

EXAMPLE 3

Figures 4A, 4B:
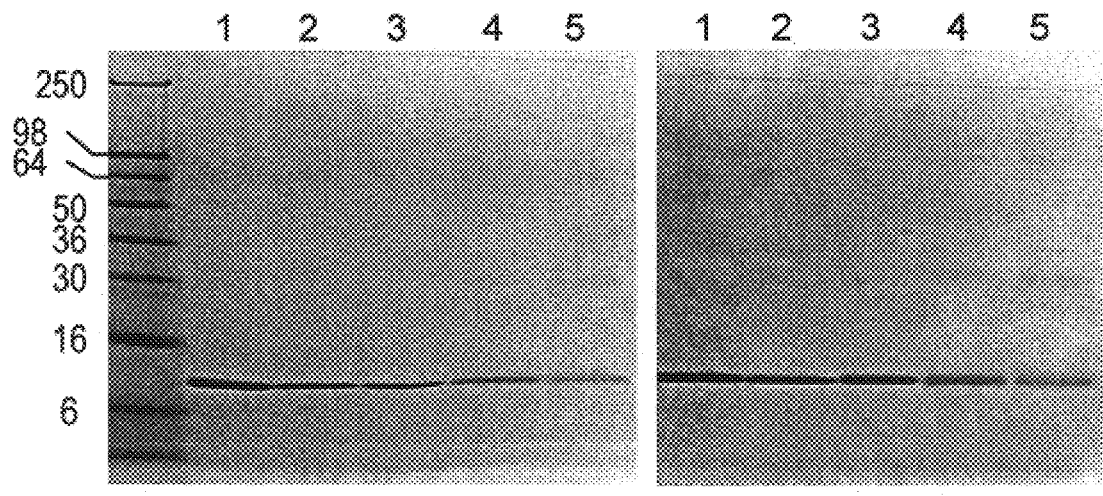
FIG. 4 provides an analysis of chemically modified MIF using reducing (A), and non-reducing (B) SDS-PAGE (18% acrylamide) analysis of human MIF treated with compound 4. For FIGS. 4(A) and 4(B), MIF (0.36 mg/mL) was either untreated (lane 1), or treated for 15 minutes with DMSO (the solvent for compound 4, lane 2, 0% enzyme inhibition), 49.5 μM compound 4 (lane 3, 37% enzyme inhibition), 190 μM compound 4 (lane 4, 94% enzyme inhibition), and 500 μM compound 4 (lane 5, 100% enzyme inhibition). Molecular masses (in kDa) of standard proteins are shown in (A).
FIGS. 4(C) and 4(D) show MALDI mass spectra of unmodified recombinant human MIF (predicted molecular mass 12.345 kDa), and recombinant human MIF (360 μg/mL that was incubated with 200 μM compound 4), respectively. The predicted masses for 1:1 (12.494 kDa) and 1:2 (12.643 kDa) MIF+compound 4 covalent adducts is within 3 atomic mass units of the measured masses at 12.491 kDa and 12.645 kDa, respectively. The data show that compound 4 modifies MIF chemically to form a stable, covalent conjugates.
Figure 4D:
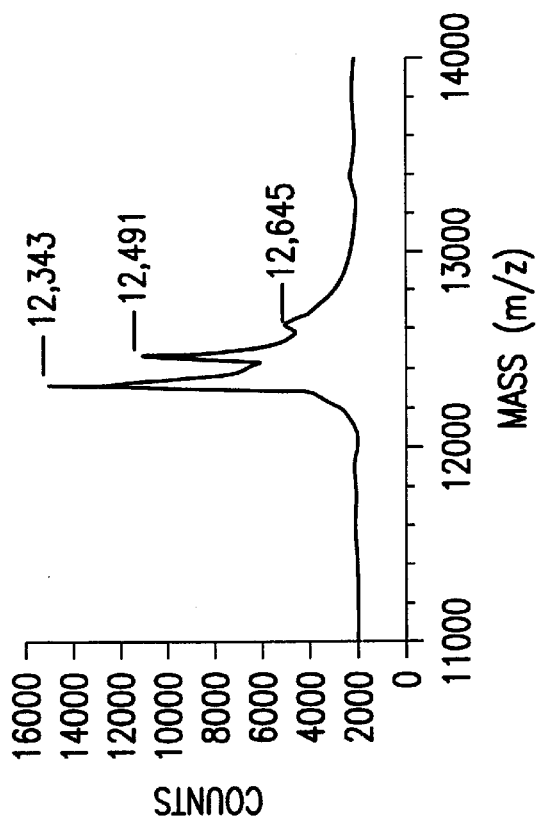
Figure 4C:
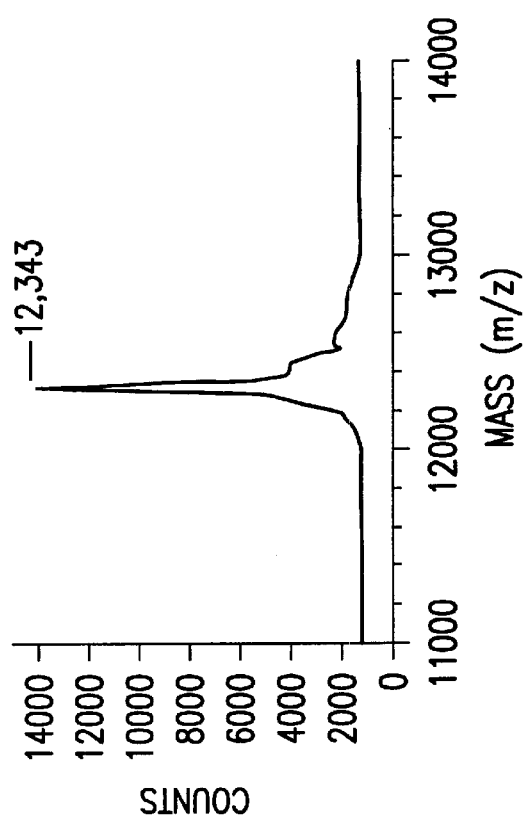

Covalent Enzyme Modification. This example shows that NAPQI (4) modifies MIF chemically to form a stable, covalent MIF-NAPQI conjugate (see FIG. 4). Compound 4 has previously been reported to react with protein nucleophiles and induce protein-protein crosslinking (Dahlin & Nelson, *J. Med. Chem.*, 25:885–886, 1982; Chen et al., *Chem. Res. Toxicol.* 11:295–301, 1998). Analysis of reaction products by SDS-PAGE indicated that at concentrations of compound 4 that led to 94% MIF enzyme inhibition (190 μM), there were small amounts of a 25 kDa species, consistent with the presence of crosslinked MIF monomers (see FIG. 4a and 4b, lanes 4). These results, and the fact that it was not possible to restore enzymatic activity by dialyzing or gel filtering MIF that was inactivated with compound 4 (data not shown), indicate the formation of a covalent adduct.

Covalent modification of MIF by compound 4 was confirmed by mass spectroscopy. MIF was chemically modified with compound 4 under conditions that led to 69% inhibition of enzymatic activity. The resulting protein was then analyzed by MALDI mass spectrometry. The experimentally measured mass for MIF was 12,343 Daltons (FIG. 4C), which is within 2 mass units of the theoretical molecular mass of 12,345 Daltons. New molecular entities having molecular masses of 12,491 and 12,645 Daltons were formed in the chemically treated MIF sample (see FIG. 4D), corresponding to adducts having one and two molecules of compound 4 per MIF subunit (theoretical masses of 12,494 and 12,643), respectively. Additionally, a complete investigation of the MIF-NAPQI (4) adduct by liquid chromatography-electrospray ionization mass spectrometry (LC-ESIMS) showed that the molecular ion of the adduct is m/z 12491 Da, an increase of 148 Da compared to the native MIF (12343 Da) (data not shown). This implies an equimolar ratio between MIF monomer and NAPQI (MW=149).

Thus, covalent modification, like the covalent adduct formed when MIF is treated with compound 4, accounted for the activity of quinone-related compounds in MIF enzyme inhibition assays, and in biological assays (see below).

EXAMPLE 4

Biological Assay of MIF Activity. This example shows that iminoquinone- and orthoquinone-based compounds not only specifically inhibit MIF enzymatic activity, but also inhibit MIF immunoregulatory activities. As described in detail above, an assay for MIF tautomerase activity that is predictive of biological MIF inhibitory activity in vivo was used to evaluate the test compounds. Briefly, the assay procedure involved measuring MIF tautomerase activity in the presence of test compound (potential inhibitors) using an L-dopachrome methyl ester as substrate. Various concentrations of inhibitor compounds were added and an IC$_{50}$ determined for enzyme (tautomerase) inhibitory activity. These IC$_{50}$ values are reported in connection with the structural diagrams of the test compounds in Table I.

These compounds are additionally assessed for inhibition of MIF biological activities in any of a number of assays for MIF biological activity including, for example, inhibition of MIF binding to target cells, inhibition of MIF release or synthesis, inhibition of MIF immunoreactivity with MIF-specific antibodies, alterations of MIF conformation or structural integrity as assessed by circular dichroism spectroscopy or thermal stability measurement, inhibition of the pro-proliferative effects of MIF on quiescent NIH/3T3 cells and inhibition of the associated prolonged ERK activation therein, inhibition of MIF-induced arachadonic acid release from NIH/3T3 cells, inhibition of MIF-induced fructose 2,6 bisphosphate formation in L6 myocytes, inhibition of MIF toxicity in TNF or LPS-challenged test animals, inhibition of the glucocorticoid counter-regulatory activity of MIF in vitro or in vivo, and inhibition of morbidity or mortality in any of a number of animal models of human diseases that are characterized by the release, production and/or appearance of MIF.

Accordingly, NAPQI (4) (i.e., MIF-NAPQI (4) conjugate) was tested in assays for: (i) induction of fructose-2,6-bisphosphate production; (ii) induction of arachidonic acid release from NIH/3T3 cells; and (iii) cross-reactivity with anti-MIF antibodies. Compound 6 (i.e., MIF-N-acetyl-3-hydroxy-p-benzoquinone imine (6) conjugate) was also tested in assays for its activity to induce fructose-2,6-bisphosphate production.

(i) Induction of fructose-2,6-bisphosphate production. Conjugates of MIF with either compound 4 or 6 (i.e., MIF-NAPQI (4) conjugate or MIF-N-acetyl-3-hydroxy-p-benzoquinone imine (6) conjugate, respectively) failed to induce fructose-2,6-bisphosphate (F2,6BP) production in L6 rat myoblasts. F2,6BP is a potent allosteric stimulator of glycolysis (see e.g., Chesney et al., *Proc. Natl. Acad. Sci. U. S. A.*, 96:3047–3052, 1999). Production of F2,6BP from fructose 6-phosphate is catalyzed by the enzyme phosphofructokinase-2 (PFK-2) and intracellular levels of F2,6BP are a good indicator of the glycolytic state of the cell (Van Schaftingen et al., *Proc. Natl. Acad. Sci. U. S. A.*, 78:3483–3486, 1981). Inflammatory cytokines, such as TNFα, stimulate carbohydrate metabolism in vitro by enhancing the production of intracellular F2,6BP in L6 rat myocytes (Yamasaki et al., *Diabetes Res. Clin. Pract.*, 32:11–18, 1996).

Figure 5:
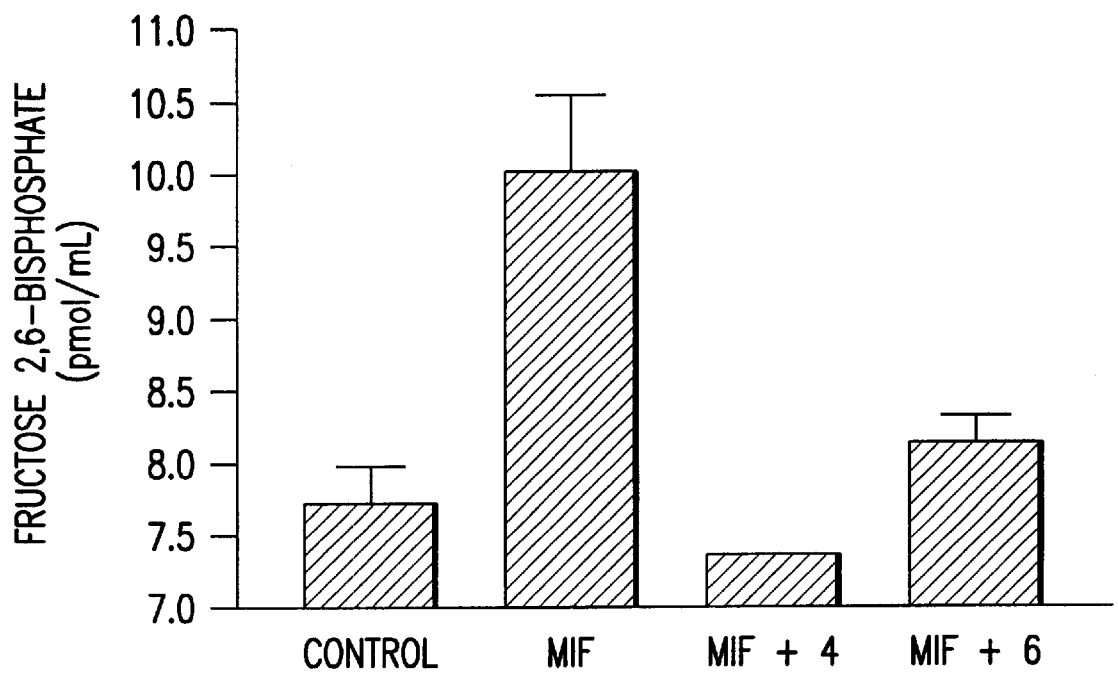
FIG. 5 shows the effects of recombinant mouse MIF samples on fructose-2,6-diphosphate (F2,6BP) production in differentiated L6 muscle cells. The L6 cell cultures were treated with 10 ng/mL mouse MIF, or equivalent amounts of MIF that were pretreated (conjugated) with compound 4 (167 μM, 96% inhibition of enzyme activity) or compound 6 (33 μM, 100% inhibition of enzyme activity) and F2,6BP was measured in the culture supernatants. These data show that conjugates of MIF with compounds 4 or 6 fail to induce increased F2,6BP production by L6 rat myoblasts.

Interestingly, a comparable elevation of F2,6BP levels was detected when cell cultures were treated with recombinant MIF (see FIG. 5). The present induction assays were performed on L6 rat myoblasts that were treated with murine MIF at 10 ng/ml. Prior to the assay, the MIF was treated with either compound 4 (167 μM, leading to 98% enzyme inactivation) or compound 6 (33 μM, leading to 100% enzyme inactivation). As expected, non-reacted murine MIF stimulated F2,6BP production by the L6 rat myoblasts (130% of control). In contrast, the murine MIF conjugates formed upon treatment of MIF with compound 4 or 6 were not significantly active, having 94% and 105%, respectively, of the activity of untreated mouse MIF (control=100%).

Thus, quinone-like MIF inhibitors, such as compounds 4 and 6, not only inhibited the tautomerase enzymatic activity of MIF, but also inhibited MIF biological activity in a bioassay that is further predictive of therapeutic utility.

(ii) Induction of arachidonic acid release from NIH/3T3 cells. MIF-NAPQI (4) conjugate did not induce arachidonic acid release from NIH/3T3 cells (see FIG. 6). MIF stimulates the proliferation of NIH3T3 cells, apparently via signaling pathways associated with the phosphorylation and activation of the p44/p42 extracellular-signal-regulated kinases (ERK) (Mitchell et al., *J. Biol. Chem.*, 274:18100–18106, 1999). Such MIF activation of ERK in NIH/3T3 cells is sustained for a period of at least 24 hours, contrasting sharply with the rapid termination of kinase activity that generally has been observed with growth factor mediated-signaling in these cells. Moreover, the MIF-induced activation of the MAP kinase pathway results in the phosphorylation and activation of cytoplasmic phospholipase A2 (cPLA$_2$) independent of Ca$^{2+}$ mobilization, and leads to the production of arachidonic acid in a time- and concentration-dependent fashion. This profile of cellular proliferation and signaling activity was used to evaluate the inhibition of MIF bioactivity by NAPQI and other candidate inhibitors.

The effect of MIF-NAPQI (4) conjugate on arachidonic acid release was tested by adding equivalent amounts of either MIF or MIF-NAPQI (4) conjugate to NIH3/3T3 cell cultures that had been pre-equilibrated with radioactive arachidonate, followed by the measurement of arachidonic acid release by scintillation counting. Briefly, NIH/3T3 fibroblasts were labeled with 1 μM [$^{14}$C]-arachidonic acid. After overnight culture, the cells were washed extensively with PBS, and the appropriate samples of MIF or MIF-NAPQI (4) conjugate were added in duplicate. The release of arachidonic acid into medium was then measured as described previously (Mitchell et al., *J. Biol. Chem.*, 274:18100–18106, 1999).

Figure 6:
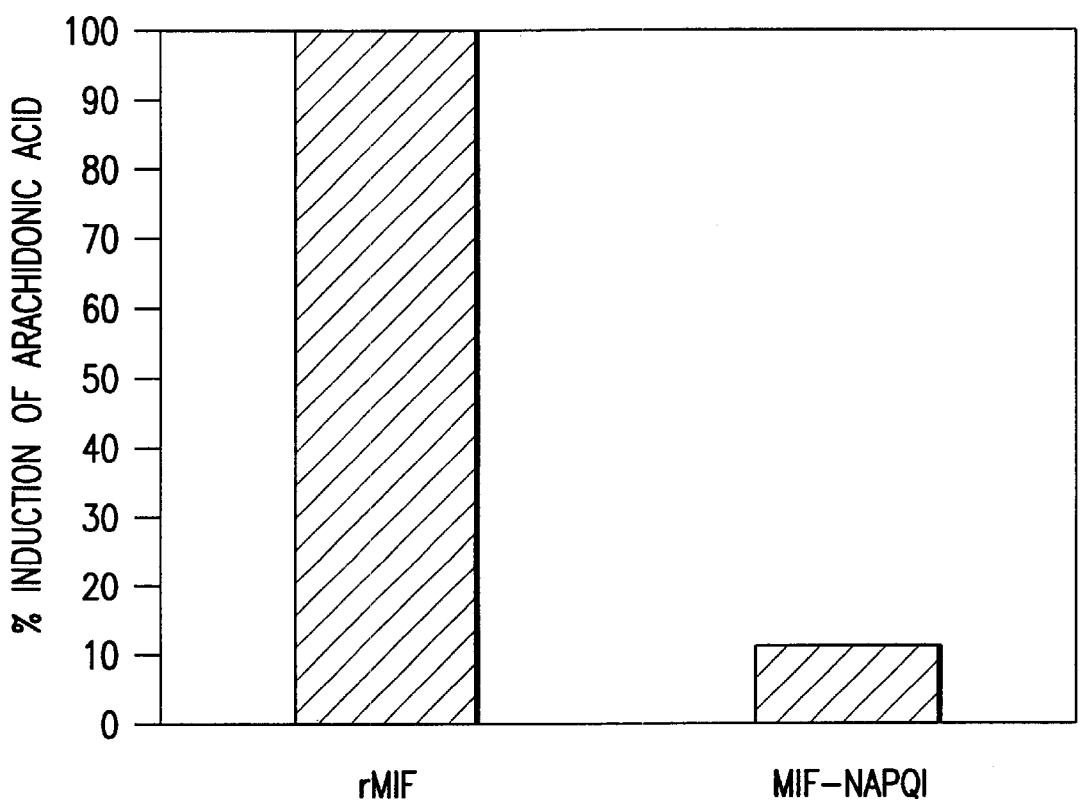
FIG. 6 shows the effect of NAPQI (4) on the MIF-mediated induction of cellular arachidonic acid release.

Cultures treated with the stable MIF-NAPQI (4) conjugate elaborated less than 1/10 as much arachidonic acid into the culture supernatants as did cultures treated with MIF, indicating that this cellular activity of MIF is profoundly inhibited by the molecular changes induced by covalent addition of NAPQI (FIG. 6).

(iii) Cross-reactivity with anti-MIF antibodies. Monoclonal anti-human MIF antibodies (clone # 12302.2, R&D, Minneapolis, Minn.) fail to recognize the stable MIF-NAPQI (4) conjugate. Without being bound by mechanism, and in view of the lack of bioactivity of the MIF-NAPQI (4) conjugate in the above arachidonic acid release and F2,6BP induction assays, it is likely that NAPQI (4) conjugation induces distortion of the MIF peptide conformation. This distortion also renders the MIF-NAPQI (a) (4) conjugate non-crossreactive with anti-MIF Mab.

The presence of such structural changes was further explored by characterizing the binding of additional MIF-specific antibodies (Picower Institute clones XIV. 14.3, III.D.9 and XIV. 15.5, which differ in their epitope recognition and activity to inhibit biologically active MIF), using a standard ELISA technique. In a standardized sandwich ELISA specific for MIF Meinhardt et al., *Endocrinology*, 137:5090–5095, 1996), an equivalent amount of MIF-NAPQI (4) conjugate (as indicated by protein concentration) was recognized 7-fold less than purified recombinant MIF that had not been exposed to NAPQI (4) (FIG. 7). Again, without being bound by mechanism, this loss of cross-reactivity of MIF-NAPQI (4) was most likely due to remote structural changes in MIF induced by covalent attachment of NAPQI (4). These structural changes might, in turn, account for the lack of bioactivities of MIF-NAPQI (4) and MIF-N-acetyl-3-hydroxy-p-benzoquinone imine (6) conjugates in the F2,6BP induction assay, and for the lack of bioactivity of MIF-NAPQI (4) conjugate in the arachidonic acid release assay.

Thus, inhibition by a compound in the tautomerase assay is predictive of its utility to inhibit MIF biological activity including its therapeutic use in this regard, because quinone-based reagents such as compounds 4 and 6 not only inhibited the tautomerase enzymatic activity of MIF, but also inhibited MIF biological activity in bioassays that are further predictive of therapeutic utility.

Based on the examples of the present invention, and without being bound by theory, quinone-based compounds (described herein by formulas I and II) can derivatize MIF covalently. Such derivatization inhibits MIF tautomerase activity and induces critical changes in the native MIF protein surface, as indicated by the loss of the cross-reactivity with monoclonal anti-MIF antibodies, and the loss of MIF bioactivity in bioassays that are further predictive of therapeutic utility.

In conclusion, two related genera of MIF enzyme inhibitors, comprising either iminoquinone or orthoquinone ring systems, are low molecular weight agents that irreversibly inhibit both MIF enzymatic and biological activities by forming stable covalent interactions with MIF amino acid residues. These agents are accordingly useful as pharmaceutical compositions to inhibit MIF activities in the clinical setting.

We claim:

1. A pharmaceutical composition comprising a quinone compound, or a pharmaceutically acceptable salt thereof, and a pharmaceutically acceptable carrier or diluent, said compound having the formula I or II wherein formula I is:

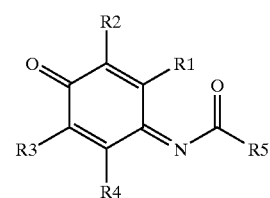

wherein $R_1$, $R_2$, $R_3$, and $R_4$ are independently H, CH$_3$, CH$_2$CH$_3$, OH, OCH$_3$, OCH$_2$CH$_3$, Br, Cl, F, or I and $R_5$ is independently H, CH$_3$, CH$_2$CH$_3$, OH, OCH$_3$, OCH$_2$CH$_3$, or wherein $R_6$ and $R_7$ are independently H or C$_{1-4}$alkyl; and wherein formula II is:

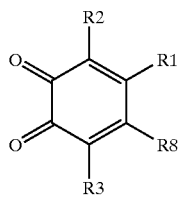

wherein $R_1$, $R_2$ and $R_3$ are defined as for formula I and $R_8$ is (CH=CH)$_n$—CO—$R_5$ wherein n=0, 1, 2, or 3 and $R_5$ is defined in formula I with the proviso that said compound is not a compound having formula I wherein either
(a) $R_1$, $R_2$, $R_3$, and $R_4$ are all H, and $R_5$ is $CH_3$; or
(b) $R_1$, $R_3$, and $R_4$ are all H, $R_2$ is $OCH_3$ and $R_5$ is $CH_3$.

2. The pharmaceutical composition of claim 1 wherein for formula I: $R_5$ is $CH_3$; and $R_1$, $R_2$, $R_3$, and $R_4$ are independently H, OH, $CH_3$, $OCH_3$, or $OCH_2CH_3$ with the proviso that the compound in formula I is not a compound having formula I wherein either
(a) $R_1$, $R_3$, and $R_4$ are all H, and $R_5$ is $CH_3$; or
(b) $R_1$, $R_3$, and $R_4$ are all H, $R_2$ is $OCH_3$ and is $CH_3$.

3. The pharmaceutical composition of claim 2 wherein for formula I: $R_5$ is $CH_3$; $R_1$ and $R_4$ are H; and $R_2$ and $R_3$, and $R_4$ independently are H, OH, $CH_3$, $OCH_3$, or $OCH_2CH_3$ with proviso that the compound in formula I is not a compound having formula I wherein either
(a) $R_1$, $R_2$, $R_3$, and $R_4$ are all H, and $R_5$ is $CH_3$; or
(b) $R_1$, $R_3$, and $R_4$ are all H, $R_2$ is $OCH_3$ and $R_5$ is $CH_2$.

4. The pharmaceutical composition of claim 3 wherein for formula I: $R_5$ is $CH_3$; $R_1$, $R_2$ and $R_4$ are H; and $R_3$ is OH.

5. The pharmaceutical composition of claim 1 wherein for formula II: n is 1 and $R_5$ is OH; and $R_1$, $R_2$ and $R_3$, independently are H, OH, $CH_3$, $OCH_3$ or $OCH_2CH_3$.

6. The pharmaceutical composition of claim 5 wherein for formula II: n is 1 and $R_5$ is OH; $R_1$ is H; and $R_2$ and $R_3$, independently are H, OH, $CH_3$, $OCH_3$ or $OCH_2CH_3$.

7. The pharmaceutical composition of claim 6 wherein for formula II: n is 1 and $R_5$ is OH; and $R_1$, $R_2$ and $R_3$ are H.

8. The pharmaceutical composition of claim 1 further comprising a steroid, a glucocorticoid, anti-TNFα antibody, anti-IL-1 antibody, anti-IFN-γ antibody, IL-1RA, IL-10 or combinations thereof.

9. A pharmaceutical composition comprising a quinone compound, or a pharmaceutically acceptable salt thereof, and a pharmaceutically acceptable carrier or diluent, wherein the compound forms a stable covalent interaction with an amino acid residue of an MIF protein with the proviso that said compound is not a compound having formula I:

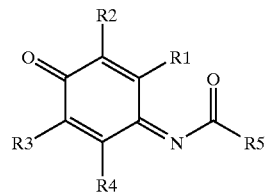

wherein either
(a) $R_1$, $R_2$, $R_3$, and $R_4$ are all H, and $R_5$ is $CH_3$; or
(b) $R_1$, $R_3$, and $R_4$ are all H, $R_2$ is $OCH_3$ and $R_5$ is $CH_3$.

10. The pharmaceutical composition of claim 9 wherein the compound is a substituted iminoquinone compound or a substituted orthoquinone compound.

11. The pharmaceutical composition of claim 9 further comprising a steroid, a glucocorticoid, anti-TNFα antibody, anti-IL-1 antibody, anti-IFN-γ antibody, IL-1RA, IL-10 or combinations thereof.

* * * * *